US010287562B2

(12) United States Patent
Andersen et al.

(10) Patent No.: US 10,287,562 B2
(45) Date of Patent: May 14, 2019

(54) ALICYCLOBACILLUS VARIANTS AND POLYNUCLEOTIDES ENCODING SAME

(71) Applicant: NOVOZYMES A/S, Bagsvaerd (DK)

(72) Inventors: Carsten Andersen, Vaerloese (DK); Iben Damager, Valby (DK); Astrid Munch, Frederiksberg (DK); Tine Hoff, Holte (DK)

(73) Assignee: NOVOSZYMES A/S, Bagsvaerd (DK)

( * ) Notice: Subject to any disclaimer, the term of this patent is extended or adjusted under 35 U.S.C. 154(b) by 0 days.

(21) Appl. No.: 15/527,593

(22) PCT Filed: Nov. 20, 2015

(86) PCT No.: PCT/EP2015/077236
§ 371 (c)(1),
(2) Date: May 17, 2017

(87) PCT Pub. No.: WO2016/079305
PCT Pub. Date: May 26, 2016

(65) Prior Publication Data
US 2017/0321199 A1  Nov. 9, 2017

(30) Foreign Application Priority Data

Nov. 20, 2014  (EP) .................................. 14194140
Nov. 20, 2014  (EP) .................................. 14194152

(51) Int. Cl.
*C12N 9/28* (2006.01)
*C11D 3/386* (2006.01)
*C12N 9/00* (2006.01)

(52) U.S. Cl.
CPC ............ *C12N 9/2417* (2013.01); *C11D 3/386* (2013.01); *C12Y 302/01001* (2013.01); *C12N 9/00* (2013.01)

(58) Field of Classification Search
CPC ........ C12N 9/2417; C12N 9/00; C11D 3/386; C12Y 302/01001
See application file for complete search history.

(56) References Cited

U.S. PATENT DOCUMENTS

| 6,093,562 A * | 7/2000 | Bisgård-Frantzen ..................... C11D 3/38681 435/202 |
| 6,482,628 B1 * | 11/2002 | Poulose ................. A23G 4/123 435/221 |
| 8,273,348 B2 * | 9/2012 | Svendsen ................. C12N 9/20 424/94.2 |

FOREIGN PATENT DOCUMENTS

| WO | 95/26397 A1 | 10/1995 |
| WO | 96/23873 A1 | 8/1996 |
| WO | 00/60058 A2 | 10/2000 |
| WO | 00/60060 A2 | 10/2000 |
| WO | 2011/076697 A1 | 6/2011 |
| WO | 2013/001078 A1 | 1/2013 |
| WO | 2014/183921 A1 | 11/2014 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1990).*
Boer et al, 1997, EBI accession No. AAW12115.
Boer et al, 1997, EBI accession No. AAW12116.
Schoonjans et al, 1997, EBI accession No. AAW12133.
Wang et al, 2013, Int Sys Evol Microbiol 63(9), 3138-3142.
Wang et al, 2014, UniProt No. A0A074LY65.

* cited by examiner

*Primary Examiner* — Ganapathirama Raghu
(74) *Attorney, Agent, or Firm* — David Fazzolare

(57) ABSTRACT

The present invention relates to alpha-amylase variants. The present invention also relates to polynucleotides encoding the variants; nucleic acid constructs, vectors, and host cells comprising the polynucleotides; and methods of using the variants.

31 Claims, 2 Drawing Sheets
Specification includes a Sequence Listing.

```
                        1                                           50
SEQ ID NO: 3    (1)   TFAGDNGTMMQYFEWYLPNDGTLWTKMGSDASHLKSIGITGVWFPPAYKG

SEQ ID NO:11    (1)   HHNGTNGTMMQYFEWYLPNDGNHWNRLNSDASNLKSKGITAVWIPPAWKG 51                                          100
SEQ ID NO: 3   (51)   QSQSDVGYGVYDMYDLGEFNQKGTVRTKYGTKAQLQSAITSLHNNGIQAY

SEQ ID NO:11   (51)   ASQNDVGYGAYDLYDLGEFNQKGTVRTKYGTRSQLQAAVTSLKNNGIQVY 101                                          150
SEQ ID NO: 3  (101)   GDVVLNHRMGADATETISAVEVNPSNRNQVTSGAYNISAWTDFEFPGRGN

SEQ ID NO:11  (101)   GDVVMNHKGGADATEMVRAVEVNPNNRNQEVTGEYTIEAWTRFDFPGRGN 151                                          200
SEQ ID NO: 3  (151)   TYSSFKWHSYYFDGVDWDQSRQLSGKIYQIQGKAWDWEVDSENGNYDYLM

SEQ ID NO:11  (151)   THSSFKWRWYHFDGVDWDQSRRLNNRIYKFRGKAWDWEVDTENGNYDYLM 201                                          250
SEQ ID No 3   (201)   GADIDYDHPDVQTEVKNWGKWFVNTLNLDGVRLDAVKHIKFDYMSSWLSS

SEQ ID NO:11  (199)   YADIDMDHPEVVNELRNWGVWYTNTLGLDGFRIDAVKHIKYSFTRDWINH 251                                          300
SEQ ID NO: 3  (251)   VKSTTGKSNLFAVGEYWNTSLGALENYENKTNWSMSLFDVPLHMNFQAAA

SEQ ID NO:11  (249)   VRSATGK-NMFAVAEFWKNDLGAIENYLQKTNWNHSVFDVPLHYNLYNAS
```

Figure 1

```
              301                                               350
SEQ ID NO: 3  (301) NGGGYYDMRNLLNNTMMKNHPIQAVTFVDNHDTEPGQALQSWVSDWFKPL

SEQ ID NO:11  (298) KSGGNYDMRNIFNGTVVQRHPSHAVTFVDNHDSQPEEALESFVEEWFKPL 351                                               400
SEQ ID NO: 3  (351) AYATILTRQEGYPCVFYGDYYGIPSQSVSAKSTWLDKQLSARKSYAYGTQ

SEQ ID NO:11  (348) AYALTLTREQGYPSVFYGDYYGIPTHGVPAMRSKIDPILEARQKYAYGPQ 401                                               450
SEQ ID NO: 3  (401) HDYLDNQDVIGWTREGDSAHAGSGLATVMSDGPGGSKTMYVGTAHAGQVF

SEQ ID NO:11  (398) HDYLDHPDVIGWTREGDSSHPKSGLATLITDGPGGSKRMYAGLKNAGETW 451                      484
SEQ ID NO: 3  (451) KDITGNRTDTVTINSAGNGTFPCNGGSVSIWVKQ

SEQ ID NO:11  (448) YDITGNRSDTVKIGSDGWGEFHVNDGSVSIYVQK
```

Figure 1 cont.

```
                      SEQUENCE LISTING

<160> NUMBER OF SEQ ID NOS: 13

<210> SEQ ID NO 1
<211> LENGTH: 1539
<212> TYPE: DNA
<213> ORGANISM: Alicyclobacillus sp.

<400> SEQUENCE: 1
atgaaaatcc gcaacggttg aaaaaaaacc ttgacgctgt tatttgcgct catcttcttg        60
ctgcctcatt ctgcagccgc gacctttgcc ggggacaacg gcacgatgat gcaatacttt       120
gaatggtatc tgcccaacga cgggacgctt tggaccaaga tgggcagcga cgcgtcgcac       180
ctgaagtcga tcgggatcac cggcgtctgg ttcccgccgg cgtacaaagg ccaatcgcag       240
tcggacgtcg gctacggcgt atacgacatg tacgacctcg gcgaattcaa ccaaaaagga       300
accgtccgca ccaagtacgg caccaaagcc cagctccaat cggcgatcac ctccctgcac       360
aacaacggca tccaagccta cggggacgtc gtcctcaacc accgcatggg cgccgatgcg       420
acggagacga tctccgccgt ggaagtcaac ccgtccaacc gcaaccaagt cacctccggg       480
gcttacaaca tctccgcttg gaccgacttc gaattcccgg gccgcggcaa cacctactcc       540
tcgtttaagt ggcactccta ctactttgac ggcgtggact gggaccaatc ccgccagctg       600
agcggcaaga tctaccagat ccaaggcacc ggcaaagcgt gggactggga agtcgattcc       660
gaaaacggca actacgacta cctgatgggc gcggacatcg actacgacca cccggacgtg       720
caaacggaag tgaagaactg gggcaagtgg ttcgtcaaca ccctcaacct cgacggcgtg       780
cgcctcgacg cggtcaagca catcaagttc gactacatgt cttcctggct gtccagcgtc       840
aaatccacga ccggcaagtc caacctgttc gccgtcggcg aatactggaa cacctcgctc       900
ggagcgctgg agaactacga gaacaaaacc aactggagca tgtcgctgtt cgacgtgccg       960
ctgcacatga acttccaagc ggcagcgaac ggcggcggct actatgatat gcgcaacctg      1020
ctcaacaaca cgatgatgaa aaatcacccg atccaagcgg tcaccttcgt cgacaaccac      1080
gacaccgagc cgggccaagc cctgcaatcg tgggtatccg actggttcaa accgctggcc      1140
tacgcgacga tcctgacccg tcaagaaggc tacccgtgcg tgttctacgg cgactactac      1200
ggcatcccgt cgcaaagcgt ctccgcgaaa tccacctggt tggacaagca gctttccgca      1260
cgcaaatcct acgcgtacgg cacccagcac gactacttgg acaaccaaga cgtgatcggc      1320
tggacgcgcg aaggcgattc cgcgcacgcg gctcgggtc ttgccaccgt catgtcggac      1380
ggccctggcg gctccaagac gatgtacgtc ggcaccgccc atgccggcca agtcttcaag      1440
gacatcaccg gcaaccgcac cgacaccgtc acgatcaact ccgcaggcaa cggcaccttc      1500
ccctgcaacg gcggctccgt ctcgatctgg gtcaaacaa                              1539
```

```
<210> SEQ ID NO 2
<211> LENGTH: 511
<212> TYPE: PRT
<213> ORGANISM: Alicyclobacillus sp.

<400> SEQUENCE: 2

Met Lys Ile Arg Asn Gly Trp Lys Lys Thr Leu Thr Leu Leu Phe Ala
1               5                   10                  15

Leu Ile Phe Leu Leu Pro His Ser Ala Ala Thr Phe Ala Gly Asp
                20                  25                  30

Asn Gly Thr Met Met Gln Tyr Phe Glu Trp Tyr Leu Pro Asn Asp Gly
                35                  40                  45

Thr Leu Trp Thr Lys Met Gly Ser Asp Ala Ser His Leu Lys Ser Ile
            50                  55                  60

Gly Ile Thr Gly Val Trp Phe Pro Pro Ala Tyr Lys Gly Gln Ser Gln
65              70                  75                  80

Ser Asp Val Gly Tyr Gly Val Tyr Asp Met Tyr Asp Leu Gly Glu Phe
                85                  90                  95

Asn Gln Lys Gly Thr Val Arg Thr Lys Tyr Gly Thr Lys Ala Gln Leu
                100                 105                 110

Gln Ser Ala Ile Thr Ser Leu His Asn Gly Ile Gln Ala Tyr Gly
            115                 120                 125

Asp Val Val Leu Asn His Arg Met Gly Ala Asp Ala Thr Glu Thr Ile
            130                 135                 140

Ser Ala Val Glu Val Asn Pro Ser Asn Arg Asn Gln Val Thr Ser Gly
145                 150                 155                 160

Ala Tyr Asn Ile Ser Ala Trp Thr Asp Phe Glu Phe Pro Gly Arg Gly
                165                 170                 175

Asn Thr Tyr Ser Ser Phe Lys Trp His Ser Tyr Tyr Phe Asp Gly Val
                180                 185                 190

Asp Trp Asp Gln Ser Arg Gln Leu Ser Gly Lys Ile Tyr Gln Ile Gln
                195                 200                 205

Gly Lys Ala Trp Asp Trp Glu Val Asp Ser Glu Asn Gly Asn Tyr Asp
            210                 215                 220

Tyr Leu Met Gly Ala Asp Ile Asp Tyr Asp His Pro Asp Val Gln Thr
225                 230                 235                 240

Glu Val Lys Asn Trp Gly Lys Trp Phe Val Asn Thr Leu Asn Leu Asp
                245                 250                 255

Gly Val Arg Leu Asp Ala Val Lys His Ile Lys Phe Asp Tyr Met Ser
                260                 265                 270

Ser Trp Leu Ser Ser Val Lys Ser Thr Thr Gly Lys Ser Asn Leu Phe
            275                 280                 285

Ala Val Gly Glu Tyr Trp Asn Thr Ser Leu Gly Ala Leu Glu Asn Tyr
            290                 295                 300

Glu Asn Lys Thr Asn Trp Ser Met Ser Leu Phe Asp Val Pro Leu His
305                 310                 315                 320

Met Asn Phe Gln Ala Ala Ala Asn Gly Gly Gly Tyr Tyr Asp Met Arg
                325                 330                 335

Asn Leu Leu Asn Asn Thr Met Met Lys Asn His Pro Ile Gln Ala Val
            340                 345                 350

Thr Phe Val Asp Asn His Asp Thr Glu Pro Gly Gln Ala Leu Gln Ser
            355                 360                 365

Trp Val Ser Asp Trp Phe Lys Pro Leu Ala Tyr Ala Thr Ile Leu Thr
            370                 375                 380
```

```
Arg Gln Glu Gly Tyr Pro Cys Val Phe Tyr Gly Asp Tyr Tyr Gly Ile
385                 390                 395                 400

Pro Ser Gln Ser Val Ser Ala Lys Ser Thr Trp Leu Asp Lys Gln Leu
            405                 410                 415

Ser Ala Arg Lys Ser Tyr Ala Tyr Gly Thr Gln His Asp Tyr Leu Asp
            420                 425                 430

Asn Gln Asp Val Ile Gly Trp Thr Arg Glu Gly Asp Ser Ala His Ala
            435                 440                 445

Gly Ser Gly Leu Ala Thr Val Met Ser Asp Gly Pro Gly Gly Ser Lys
        450                 455                 460

Thr Met Tyr Val Gly Thr Ala His Ala Gly Gln Val Phe Lys Asp Ile
465                 470                 475                 480

Thr Gly Asn Arg Thr Asp Thr Val Thr Ile Asn Ser Ala Gly Asn Gly
            485                 490                 495

Thr Phe Pro Cys Asn Gly Gly Ser Val Ser Ile Trp Val Lys Gln
            500                 505                 510

<210> SEQ ID NO 3
<211> LENGTH: 484
<212> TYPE: PRT
<213> ORGANISM: Alicyclobacillus sp.

<400> SEQUENCE: 3

Thr Phe Ala Gly Asp Asn Gly Thr Met Met Gln Tyr Phe Glu Trp Tyr
1               5                   10                  15

Leu Pro Asn Asp Gly Thr Leu Trp Thr Lys Met Gly Ser Asp Ala Ser
            20                  25                  30

His Leu Lys Ser Ile Gly Ile Thr Gly Val Trp Phe Pro Pro Ala Tyr
        35                  40                  45

Lys Gly Gln Ser Gln Ser Asp Val Gly Tyr Gly Val Tyr Asp Met Tyr
    50                  55                  60

Asp Leu Gly Glu Phe Asn Gln Lys Gly Thr Val Arg Thr Lys Tyr Gly
65                  70                  75                  80

Thr Lys Ala Gln Leu Gln Ser Ala Ile Thr Ser Leu His Asn Asn Gly
                85                  90                  95

Ile Gln Ala Tyr Gly Asp Val Val Leu Asn His Arg Met Gly Ala Asp
            100                 105                 110

Ala Thr Glu Thr Ile Ser Ala Val Glu Val Asn Pro Ser Asn Arg Asn
        115                 120                 125

Gln Val Thr Ser Gly Ala Tyr Asn Ile Ser Ala Trp Thr Asp Phe Glu
    130                 135                 140

Phe Pro Gly Arg Gly Asn Thr Tyr Ser Ser Phe Lys Trp His Ser Tyr
145                 150                 155                 160

Tyr Phe Asp Gly Val Asp Trp Asp Gln Ser Arg Gln Leu Ser Gly Lys
                165                 170                 175

Ile Tyr Gln Ile Gln Gly Lys Ala Trp Asp Trp Glu Val Asp Ser Glu
            180                 185                 190

Asn Gly Asn Tyr Asp Tyr Leu Met Gly Ala Asp Ile Asp Tyr Asp His
        195                 200                 205

Pro Asp Val Gln Thr Glu Val Lys Asn Trp Gly Lys Trp Phe Val Asn
    210                 215                 220

Thr Leu Asn Leu Asp Gly Val Arg Leu Asp Ala Val Lys His Ile Lys
225                 230                 235                 240

Phe Asp Tyr Met Ser Ser Trp Leu Ser Ser Val Lys Ser Thr Thr Gly
                245                 250                 255
```

```
Lys Ser Asn Leu Phe Ala Val Gly Glu Tyr Trp Asn Thr Ser Leu Gly
                260                 265                 270

Ala Leu Glu Asn Tyr Glu Asn Lys Thr Asn Trp Ser Met Ser Leu Phe
            275                 280                 285

Asp Val Pro Leu His Met Asn Phe Gln Ala Ala Asn Gly Gly Gly
        290                 295                 300

Tyr Tyr Asp Met Arg Asn Leu Leu Asn Asn Thr Met Met Lys Asn His
305                 310                 315                 320

Pro Ile Gln Ala Val Thr Phe Val Asp Asn His Asp Thr Glu Pro Gly
                325                 330                 335

Gln Ala Leu Gln Ser Trp Val Ser Asp Trp Phe Lys Pro Leu Ala Tyr
            340                 345                 350

Ala Thr Ile Leu Thr Arg Gln Glu Gly Tyr Pro Cys Val Phe Tyr Gly
            355                 360                 365

Asp Tyr Tyr Gly Ile Pro Ser Gln Ser Val Ser Ala Lys Ser Thr Trp
        370                 375                 380

Leu Asp Lys Gln Leu Ser Ala Arg Lys Ser Tyr Ala Tyr Gly Thr Gln
385                 390                 395                 400

His Asp Tyr Leu Asp Asn Gln Asp Val Ile Gly Trp Thr Arg Glu Gly
                405                 410                 415

Asp Ser Ala His Ala Gly Ser Gly Leu Ala Thr Val Met Ser Asp Gly
            420                 425                 430

Pro Gly Gly Ser Lys Thr Met Tyr Val Gly Thr Ala His Ala Gly Gln
            435                 440                 445

Val Phe Lys Asp Ile Thr Gly Asn Arg Thr Asp Thr Val Thr Ile Asn
        450                 455                 460

Ser Ala Gly Asn Gly Thr Phe Pro Cys Asn Gly Gly Ser Val Ser Ile
465                 470                 475                 480

Trp Val Lys Gln

<210> SEQ ID NO 4
<211> LENGTH: 269
<212> TYPE: PRT
<213> ORGANISM: Bacillus lentus

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140
```

```
Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 5
<211> LENGTH: 269
<212> TYPE: PRT
<213> ORGANISM: Thermomyces lanuginosus

<400> SEQUENCE: 5

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
        50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240
```

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
        260                 265

<210> SEQ ID NO 6
<211> LENGTH: 485
<212> TYPE: PRT
<213> ORGANISM: Bacillus sp.

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

```
Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Ser Val Ser
465                 470                 475                 480

Ile Trp Val Asn Lys
            485

<210> SEQ ID NO 7
<211> LENGTH: 485
<212> TYPE: PRT
<213> ORGANISM: Bacillus halmapalus

<400> SEQUENCE: 7

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240
```

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
        260                 265                 270

Gly Ala Leu Glu Asn Tyr Leu Asn Lys Thr Asn Trp Asn His Ser Val
    275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 8
<211> LENGTH: 484
<212> TYPE: PRT
<213> ORGANISM: Bacillus sp.

<400> SEQUENCE: 8

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Thr Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
210                 215                 220

Asn Thr Thr Asn Ile Asp Gly Phe Arg Leu Asp Ala Val Lys His Ile
225                 230                 235                 240

Lys Tyr Thr Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 9
<211> LENGTH: 485
<212> TYPE: PRT
<213> ORGANISM: Cytophaga sp.

<400> SEQUENCE: 9

```
Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415
```

```
Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Ser Val Ser
465                 470                 475                 480

Val Trp Val Gln Gln
                485

<210> SEQ ID NO 10
<211> LENGTH: 485
<212> TYPE: PRT
<213> ORGANISM: Bacillus sp.

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
            165                 170                 175

Ile Tyr Lys Phe Arg Gly His Gly Lys Ala Trp Asp Trp Glu Val Asp
        180                 185                 190

Thr Glu Asn Gly Asn Tyr Asp Tyr Leu Met Tyr Ala Asp Ile Asp Met
    195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
        260                 265                 270

Gly Ala Ile Glu Asn Tyr Leu Gln Lys Thr Asn Trp Asn His Ser Val
    275                 280                 285

Phe Asp Val Pro Leu His Tyr Asn Leu Tyr Asn Ala Ser Lys Ser Gly
290                 295                 300
```

```
Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 11
<211> LENGTH: 483
<212> TYPE: PRT
<213> ORGANISM: Bacillus sp.

<400> SEQUENCE: 11

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
            180                 185                 190
```

Asn Gly Asn Tyr Asp Tyr Leu Met Tyr Ala Asp Ile Asp Met Asp His
                195                 200                 205

Pro Glu Val Val Asn Glu Leu Arg Asn Trp Gly Val Trp Tyr Thr Asn
210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
                260                 265                 270

Ile Glu Asn Tyr Leu Gln Lys Thr Asn Trp Asn His Ser Val Phe Asp
                275                 280                 285

Val Pro Leu His Tyr Asn Leu Tyr Asn Ala Ser Lys Ser Gly Gly Asn
290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Glu Gln Gly Tyr Pro Ser Val Phe Tyr Gly Asp
                355                 360                 365

Tyr Tyr Gly Ile Pro Thr His Gly Val Pro Ala Met Arg Ser Lys Ile
                370                 375                 380

Asp Pro Ile Leu Glu Ala Arg Gln Lys Tyr Ala Tyr Gly Pro Gln His
385                 390                 395                 400

Asp Tyr Leu Asp His Pro Asp Val Ile Gly Trp Thr Arg Glu Gly Asp
                405                 410                 415

Ser Ser His Pro Lys Ser Gly Leu Ala Thr Leu Ile Thr Asp Gly Pro
                420                 425                 430

Gly Gly Ser Lys Arg Met Tyr Ala Gly Leu Lys Asn Ala Gly Glu Thr
                435                 440                 445

Trp Tyr Asp Ile Thr Gly Asn Arg Ser Asp Thr Val Lys Ile Gly Ser
450                 455                 460

Asp Gly Trp Gly Glu Phe His Val Asn Asp Gly Ser Val Ser Ile Tyr
465                 470                 475                 480

Val Gln Lys

<210> SEQ ID NO 12
<211> LENGTH: 485
<212> TYPE: PRT
<213> ORGANISM: Bacillus sp.

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
                35                  40                  45

Lys Gly Ala Ser Gln Asn Asp Val Gly Tyr Gly Ala Tyr Asp Leu Tyr
                50                  55                  60

Asp Leu Gly Glu Phe Asn Gln Lys Gly Thr Val Arg Thr Lys Tyr Gly
65                  70                  75                  80

```
Thr Arg Asn Gln Leu Gln Ala Ala Val Thr Ala Leu Lys Ser Asn Gly
                85                  90                  95
Ile Gln Val Tyr Gly Asp Val Val Met Asn His Lys Gly Gly Ala Asp
            100                 105                 110
Ala Thr Glu Trp Val Arg Ala Val Glu Val Asn Pro Ser Asn Arg Asn
            115                 120                 125
Gln Glu Val Ser Gly Asp Tyr Thr Ile Glu Ala Trp Thr Lys Phe Asp
        130                 135                 140
Phe Pro Gly Arg Gly Asn Thr His Ser Asn Phe Lys Trp Arg Trp Tyr
145                 150                 155                 160
His Phe Asp Gly Val Asp Trp Asp Gln Ser Arg Gln Leu Gln Asn Arg
                165                 170                 175
Ile Tyr Lys Phe Arg Gly Asp Gly Lys Gly Trp Asp Trp Glu Val Asp
            180                 185                 190
Thr Glu Asn Gly Asn Tyr Asp Tyr Leu Met Tyr Ala Asp Ile Asp Met
            195                 200                 205
Asp His Pro Glu Val Val Asn Glu Leu Arg Asn Trp Gly Val Trp Tyr
        210                 215                 220
Thr Asn Thr Leu Gly Leu Asp Gly Phe Arg Ile Asp Ala Val Lys His
225                 230                 235                 240
Ile Lys Tyr Ser Phe Thr Arg Asp Trp Leu Thr His Val Arg Asn Thr
                245                 250                 255
Thr Gly Lys Asn Met Phe Ala Val Ala Glu Phe Trp Lys Asn Asp Ile
            260                 265                 270
Gly Ala Ile Glu Asn Tyr Leu Ser Lys Thr Asn Trp Asn His Ser Val
            275                 280                 285
Phe Asp Val Pro Leu His Tyr Asn Leu Tyr Asn Ala Ser Arg Ser Gly
        290                 295                 300
Gly Asn Tyr Asp Met Arg Gln Ile Phe Asn Gly Thr Val Val Gln Arg
305                 310                 315                 320
His Pro Thr His Ala Val Thr Phe Val Asp Asn His Asp Ser Gln Pro
                325                 330                 335
Glu Glu Ala Leu Glu Ser Phe Val Glu Glu Trp Phe Lys Pro Leu Ala
            340                 345                 350
Cys Ala Leu Thr Leu Thr Arg Asp Gln Gly Tyr Pro Ser Val Phe Tyr
            355                 360                 365
Gly Asp Tyr Tyr Gly Ile Pro Thr His Gly Val Pro Ala Met Lys Ser
        370                 375                 380
Lys Ile Asp Pro Ile Leu Glu Ala Arg Gln Lys Tyr Ala Tyr Gly Lys
385                 390                 395                 400
Gln Asn Asp Tyr Leu Asp His His Asn Met Ile Gly Trp Thr Arg Glu
                405                 410                 415
Gly Asn Thr Ala His Pro Asn Ser Gly Leu Ala Thr Ile Met Ser Asp
            420                 425                 430
Gly Pro Gly Gly Asn Lys Trp Met Tyr Val Gly Arg Asn Lys Ala Gly
            435                 440                 445
Gln Val Trp Arg Asp Ile Thr Gly Asn Arg Ser Gly Thr Val Thr Ile
        450                 455                 460
Asn Ala Asp Gly Trp Gly Asn Phe Ser Val Asn Gly Gly Ser Val Ser
465                 470                 475                 480
Ile Trp Val Asn Asn
            485
```

```
<210> SEQ ID NO 13
<211> LENGTH: 486
<212> TYPE: PRT
<213> ORGANISM: Alicyclobacillus sp.

<400> SEQUENCE: 13
```

| | | | | | | | | | | | | | | | |
|---|---|---|---|---|---|---|---|---|---|---|---|---|---|---|---|
| Thr | Phe | Ala | Gly | Asp | Asn | Gly | Thr | Met | Met | Gln | Tyr | Phe | Glu | Trp | Tyr |
| 1 | | | | 5 | | | | | 10 | | | | | 15 | |
| Leu | Pro | Asn | Asp | Gly | Thr | Leu | Trp | Thr | Lys | Met | Gly | Ser | Asp | Ala | Ser |
| | | | 20 | | | | | 25 | | | | | 30 | | |
| His | Leu | Lys | Ser | Ile | Gly | Ile | Thr | Gly | Val | Trp | Phe | Pro | Pro | Ala | Tyr |
| | | | 35 | | | | 40 | | | | | 45 | | | |
| Lys | Gly | Gln | Ser | Gln | Ser | Asp | Val | Gly | Tyr | Gly | Val | Tyr | Asp | Met | Tyr |
| 50 | | | | | 55 | | | | | 60 | | | | | |
| Asp | Leu | Gly | Glu | Phe | Asn | Gln | Lys | Gly | Thr | Val | Arg | Thr | Lys | Tyr | Gly |
| 65 | | | | | 70 | | | | | 75 | | | | | 80 |
| Thr | Lys | Ala | Gln | Leu | Gln | Ser | Ala | Ile | Thr | Ser | Leu | His | Asn | Asn | Gly |
| | | | | 85 | | | | | 90 | | | | | 95 | |
| Ile | Gln | Ala | Tyr | Gly | Asp | Val | Val | Leu | Asn | His | Arg | Met | Gly | Ala | Asp |
| | | | | 100 | | | | | 105 | | | | | 110 | |
| Ala | Thr | Glu | Thr | Ile | Ser | Ala | Val | Glu | Val | Asn | Pro | Ser | Asn | Arg | Asn |
| | | | 115 | | | | | 120 | | | | | 125 | | |
| Gln | Val | Thr | Ser | Gly | Ala | Tyr | Asn | Ile | Ser | Ala | Trp | Thr | Asp | Phe | Glu |
| | 130 | | | | | 135 | | | | | 140 | | | | |
| Phe | Pro | Gly | Arg | Gly | Asn | Thr | Tyr | Ser | Ser | Phe | Lys | Trp | His | Ser | Tyr |
| 145 | | | | | 150 | | | | | 155 | | | | | 160 |
| Tyr | Phe | Asp | Gly | Val | Asp | Trp | Asp | Gln | Ser | Arg | Gln | Leu | Ser | Gly | Lys |
| | | | | 165 | | | | | 170 | | | | | 175 | |
| Ile | Tyr | Gln | Ile | Gln | Gly | Thr | Gly | Lys | Ala | Trp | Asp | Trp | Glu | Val | Asp |
| | | | 180 | | | | | 185 | | | | | 190 | | |
| Ser | Glu | Asn | Gly | Asn | Tyr | Asp | Tyr | Leu | Met | Gly | Ala | Asp | Ile | Asp | Tyr |
| | | | 195 | | | | | 200 | | | | | 205 | | |
| Asp | His | Pro | Asp | Val | Gln | Thr | Glu | Val | Lys | Asn | Trp | Gly | Lys | Trp | Phe |
| | 210 | | | | | 215 | | | | | 220 | | | | |
| Val | Asn | Thr | Leu | Asn | Leu | Asp | Gly | Val | Arg | Leu | Asp | Ala | Val | Lys | His |
| 225 | | | | | 230 | | | | | 235 | | | | | 240 |
| Ile | Lys | Phe | Asp | Tyr | Met | Ser | Ser | Trp | Leu | Ser | Ser | Val | Lys | Ser | Thr |
| | | | | 245 | | | | | 250 | | | | | 255 | |
| Thr | Gly | Lys | Ser | Asn | Leu | Phe | Ala | Val | Gly | Glu | Tyr | Trp | Asn | Thr | Ser |
| | | | 260 | | | | | 265 | | | | | 270 | | |
| Leu | Gly | Ala | Leu | Glu | Asn | Tyr | Glu | Asn | Lys | Thr | Asn | Trp | Ser | Met | Ser |
| | | | 275 | | | | | 280 | | | | | 285 | | |
| Leu | Phe | Asp | Val | Pro | Leu | His | Met | Asn | Phe | Gln | Ala | Ala | Asn | Gly | |
| | 290 | | | | | 295 | | | | | 300 | | | | |
| Gly | Gly | Tyr | Tyr | Asp | Met | Arg | Asn | Leu | Leu | Asn | Asn | Thr | Met | Met | Lys |
| 305 | | | | | 310 | | | | | 315 | | | | | 320 |
| Asn | His | Pro | Ile | Gln | Ala | Val | Thr | Phe | Val | Asp | Asn | His | Asp | Thr | Glu |
| | | | | 325 | | | | | 330 | | | | | 335 | |
| Pro | Gly | Gln | Ala | Leu | Gln | Ser | Trp | Val | Ser | Asp | Trp | Phe | Lys | Pro | Leu |
| | | | 340 | | | | | 345 | | | | | 350 | | |
| Ala | Tyr | Ala | Thr | Ile | Leu | Thr | Arg | Gln | Glu | Gly | Tyr | Pro | Cys | Val | Phe |
| | | | 355 | | | | | 360 | | | | | 365 | | |
| Tyr | Gly | Asp | Tyr | Tyr | Gly | Ile | Pro | Ser | Gln | Ser | Val | Ser | Ala | Lys | Ser |
| | 370 | | | | | 375 | | | | | 380 | | | | |

-continued

```
Thr Trp Leu Asp Lys Gln Leu Ser Ala Arg Lys Ser Tyr Ala Tyr Gly
385                 390                 395                 400

Thr Gln His Asp Tyr Leu Asp Asn Gln Asp Val Ile Gly Trp Thr Arg
            405                 410                 415

Glu Gly Asp Ser Ala His Ala Gly Ser Gly Leu Ala Thr Val Met Ser
            420                 425                 430

Asp Gly Pro Gly Gly Ser Lys Thr Met Tyr Val Gly Thr Ala His Ala
            435                 440                 445

Gly Gln Val Phe Lys Asp Ile Thr Gly Asn Arg Thr Asp Thr Val Thr
        450                 455                 460

Ile Asn Ser Ala Gly Asn Gly Thr Phe Pro Cys Asn Gly Gly Ser Val
465                 470                 475                 480

Ser Ile Trp Val Lys Gln
                485
```

ALICYCLOBACILLUS VARIANTS AND POLYNUCLEOTIDES ENCODING SAME

CROSS-REFERENCE TO RELATED APPLICATIONS

This application is a 35 U.S.C. 371 national application of PCT/EP2015/077236 filed Nov. 20, 2015, which claims priority or the benefit under 35 U.S.C. 119 of European application nos. 14194152.6 and 14194140.1, both filed on Nov. 20, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to *Alicyclobacillus* variants, polynucleotides encoding the variants, methods of producing the variants, and methods of using the variants.

Description of the Related Art

Alpha-amylases have for many years been used in laundry where is it well-known that alpha-amylases have a beneficial effect in removal of starch containing stains.

WO95/26397 discloses alkaline *Bacillus* amylases having good wash performance measured at temperatures in the range of 30-60° C.

WO00/60060 and WO00/60058 discloses further bacterial alpha-amylases having good wash performance.

In recent years there has been a desire to reduce the temperature of the laundry in order to reduce the energy consumption. Lowering the temperature in laundry often means that the performance of the detergent composition and the enzyme is reduced and a lower wash performance is therefore obtained at low temperature. It is therefore desired to find new alpha-amylases having good wash performance at low temperature. Accordingly, it is an object of the present invention to provide alpha-amylases which have good wash performance at low temperature, such as at 15° C. It is another object to provide alpha-amylases which have improved wash performance in model detergent J (see below) compared to the above mentioned known alpha-amylases such as the alpha-amylase disclosed as SEQ ID NO: 2 in WO00/60060.

SUMMARY OF THE INVENTION

The present invention provides variants having alpha-amylase activity and polynucleotides encoding the polypeptides. It further provides methods of obtaining the same.

Accordingly, the present invention relates to an alpha-amylase variant, comprising a substitution at one or more positions corresponding to positions 109, 51, 201, 269, 294, 297, 298, 193, and 314 of the polypeptide according to SEQ ID NO:3, wherein the variant has alpha-amylase activity, and wherein said parent alpha-amylase has at least 89%, such as at least 90%, such as at least 91%, such as at least 92%, such as at least 93%, such as at least 94%, such as at least 95%, sequence identity to the polypeptide of SEQ ID NOs: 3 or 13.

The present invention also relates to polynucleotides encoding the variants; nucleic acid constructs, vectors, and host cells comprising the polynucleotides; and methods of producing the variants.

The invention also relates to compositions comprising the variants. In particular, detergent compositions are disclosed herein.

The present invention also relates to the use of a variant according to the invention in a cleaning process, such as laundry and hard surface cleaning.

The present invention also provides a method of obtaining a variant having alpha-amylase activity, wherein the method comprises the steps of introducing a substitution in one or more positions corresponding to positions 109, 51, 201, 269, 294, 297, 298, 193, and 314 of the polypeptide according to SEQ ID NO:3, wherein the variant has at least 67%, such as at least 70%, such as at least 75%, such as at least 80%, such as at least 85%, such as at least 90%, such as at least 95%, such as at least 96%, such as at least 97%, such as at least 99%, but less than 100% sequence identity with the amino acid sequence of SEQ ID NOs: 3 or 13, wherein the variant has alpha-amylase activity; and recovering said variant.

BRIEF DESCRIPTION OF THE FIGURES

FIG. 1 shows a sequence alignment of the amino acid sequence of SEQ ID NO: 3 and SEQ ID NO: 11.

DEFINITIONS

Alpha-amylase: The term "alpha-amylase" as used herein, refers to an enzyme that has alpha-amylase activity (EC 3.2.1.1) that hydrolyses alpha bonds of large, alpha-linked polysaccharides, such as starch and glycogen, yielding glucose and maltose. The terms "alpha-amylase" and "amylase" may be used interchangeably and constitute the same meaning and purpose within the scope of the present invention. For purposes of the present invention, alpha-amylase activity is determined according to the procedure described in the Examples. In one aspect, the variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NO: 3. The alpha-amylase activity may be determined according to a method using the Amylazyme substrate which is described in the section "Amylazyme activity assay".

Allelic variant: The term "allelic variant" as used herein, refers to any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" as used herein, refers to a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" as used herein, refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" as used herein, refers to nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" as used herein, refers to any step involved in the production of a variant including, but not limited to, transcription, post-transcriptional modification, translation, post-translational modification, and secretion.

Expression vector: The term "expression vector" as used herein, refers to a linear or circular DNA molecule that comprises a polynucleotide encoding a variant and is operably linked to control sequences that provide for its expression.

Fragment: The term "fragment" as used herein, refers to a polypeptide having one or more (e.g., several) amino acids absent from the amino and/or carboxyl terminus of a mature polypeptide; wherein the fragment has alpha-amylase activity. In one aspect, a fragment contains at least 85% of the amino acid residues of SEQ ID NO:3, at least 90% of the amino acid residues of SEQ ID NO:3, or at least 95% of the amino acid residues of SEQ ID NO:3.

High stringency conditions: The term "high stringency conditions" as used herein, refers to for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Host cell: The term "host cell" as used herein, refers to any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" as used herein, refers to a characteristic associated with a variant that is improved compared to the parent. Such improved properties include, but are not limited to, performance, such as wash performance, stability, such as stability under storage conditions.

Isolated: The term "isolated" as used herein, refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" as used herein, refers to probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Mature polypeptide: The term "mature polypeptide" as used herein, refers to a polypeptide in its final form following translation and any post-translational modifications, such as N-terminal processing, C-terminal truncation, glycosylation, phosphorylation, etc. Also contemplated within the term "mature polypeptide" is that the signal peptide of the polypeptide has been cleaved off e.g. during a nature maturation process within the cell expressing the polypeptide. In one aspect, the mature polypeptide is the amino acid sequence of SEQ ID NO:3. It is known in the art that a host cell may produce a mixture of two of more different mature polypeptides (i.e., with a different C-terminal and/or N-terminal amino acid) expressed by the same polynucleotide.

Polynucleotide coding sequence: The term "polynucleotide coding sequence" as used herein, refers to a polynucleotide that encodes a mature polypeptide having alpha-amylase activity. In one aspect, the polynucleotide coding sequence is nucleotides of SEQ ID NO: 1.

Medium stringency conditions: The term "medium stringency conditions" as used herein, refers to probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" as used herein, refers to probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" as used herein, refers to a polynucleotide encoding a variant. Thus, the terms "mutant"

and "variant" may be used interchangeably and constitute the same meaning and purpose within the present invention.

Nucleic acid construct: The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" as used herein, refers to a configuration in which a control sequence is placed at an appropriate position relative to the coding sequence of a polynucleotide such that the control sequence directs expression of the coding sequence.

Parent or parent alpha-amylase: The terms "parent" or "parent alpha-amylase" may be used interchangeably herein, both terms refer to an alpha-amylase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For the purposes of the present invention, the sequence identity between two amino acid sequences may be determined using the program Vector NTI® which is well-known in the art. Another well-known program is the ClustalW program. Thus, identification of the corresponding amino acid residue in another alpha-amylase may be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1880), and EMBOSS EMMA employing ClustalW (1.83 or later; Thompson et al., 1994, *Nucleic Acids Research* 22: 4673-4680), using their respective default parameters.

The sequence identity between two amino acid sequences may also be determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

The sequence identity between two deoxyribonucleotide sequences may also be determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Subsequence: The term "subsequence" as used herein, refers to a polynucleotide having one or more (e.g., several) nucleotides absent from the 5' and/or 3' end of a mature polypeptide coding sequence; wherein the subsequence encodes a fragment having alpha-amylase activity.

Enzyme Detergency benefit: The term "enzyme detergency benefit" used herein, refers to the advantageous effect an enzyme may add to a detergent compared to the same detergent without the enzyme. Important detergency benefits which can be provided by enzymes are stain removal with no or very little visible soils after washing and/or cleaning, prevention or reduction of re-deposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of re-deposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

Textile care benefit: The term "textile care benefits", as used herein, is defined as not being directly related to catalytic stain removal or prevention of re-deposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

Dish washing composition: The term "dish washing composition" as used herein, refers to all forms of compositions for cleaning hard surfaces. The present invention is not restricted to any particular type of dish wash composition or any particular detergent. Thus, in one embodiment, the dish washing composition is a liquid dish washing composition, a powder dish washing composition, wherein the composition may optionally be in the form of a unit dose.

Hard surface cleaning: The term "hard surface cleaning" as used herein, refers to cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

Improved wash performance: The term "improved wash performance" as used herein, refers to an improvement of the wash performance of an alpha-amylase of the present invention relative to the wash performance of the alpha-amylases known in the art. Improved wash performance may be measured by comparing of the so-called Intensity value. The improved wash performance is determined according to the section "Wash performance of alpha-amylases using Automatic Mechanical Stress Assay" and using model detergent J at 15° C. Other model detergents may be used, such as model detergent A, model detergent X or model detergent T.

Wash performance: the term "wash performance" as used herein, refers to an enzyme's ability to remove starch or starch-containing stains present on the object to be cleaned during e.g. laundry or hard surface cleaning, such as dish wash. The term "wash performance" includes cleaning in general e.g. hard surface cleaning as in dish wash, but also wash performance on textiles such as laundry, and also industrial and institutional cleaning. The wash performance may be quantified by calculating the so-called Intensity value. Wash performance may be determined as in described in the Methods section herein.

Low temperature: "Low temperature" as used herein, refers to is a temperature of 5-40° C., such as 5-35° C., preferably 5-30° C., more preferably 5-25° C., more preferably 5-20° C., most preferably 5-15° C., and in particular 5-10° C. In a preferred embodiment, "Low temperature" is a temperature of 10-35° C., preferably 10-30° C., more preferably 10-25° C., most preferably 10-20° C., and in particular 10-15° C. Most preferred, low temperature means 15° C.

Intensity value: The wash performance is measured as the brightness expressed as the intensity of the light reflected from the sample when illuminated with white light. When the sample is stained the intensity of the reflected light is lower, than that of a clean sample. Therefore, the intensity of the reflected light can be used to measure wash performance, where a higher intensity value correlates with higher wash performance. Color measurements are made with a professional flatbed scanner (Kodak iQsmart, Kodak) used to capture an image of the washed textile. To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}$$

Variant: The term "variant" means a polypeptide having alpha-amylase activity comprising an alteration, i.e., a substitution, insertion, and/or deletion, at one or more (e.g., several) positions as compared to a "parent". A substitution means replacement of the amino acid occupying a position with a different amino acid; a deletion means removal of the amino acid occupying a position; and an insertion means adding at least one (e.g. several) amino acids, e.g. 1 to 5 amino acids, adjacent to and immediately following the amino acid occupying a position. Amino acid substitutions may exchange a native amino acid for another naturally-occurring amino acid, or for a non-naturally-occurring amino acid derivative. The variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 3.

Wild-type alpha-amylase: The term "wild-type alpha-amylase" means an alpha-amylase expressed by a naturally occurring microorganism, such as a bacterium, yeast, or filamentous fungus found in nature.

Conventions for Designation of Variants

For purposes of the present invention, the polypeptide disclosed in SEQ ID NO: 3 is used to determine the corresponding amino acid residue in another alpha-amylase. The amino acid sequence of another alpha-amylase is aligned with the polypeptide disclosed in SEQ ID NO: 3, and based on the alignment, the amino acid position number corresponding to any amino acid residue in the polypeptide disclosed in SEQ ID NO: 3 is determined. In particular, FIG. 1 shows an alignment of SEQ ID NO:3 and SEQ ID NO:11 both included herein. Thus, unless otherwise explicitly stated, amino acid positions herein described are numbered according to SEQ ID NO: 3, and alignment to determine the corresponding amino acid position in other polypeptides may be needed.

Thus, identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1880), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. Multiple substitutions may alternatively be separated by "/", ",", or a " " (i.e. space), and constitute the same meaning and purpose.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*". Multiple deletions may alternatively be separated by "/", ",", or a " " (i.e. space), and constitute the same meaning and purpose.

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

Different alterations may be also be separated by "/", "," or a " " (i.e. space), and constitute the same meaning and purpose. Accordingly, the substitution of threonine at position 226 with alanine or lysine or valine, is designated as "Thr226Ala/Lys/Val" or "T226A/K/V".

DETAILED DESCRIPTION OF THE INVENTION

In one aspect, the present invention relates to variants having improved performance, in particular improved wash performance in laundry and/or dish wash, compared to the polypeptide of the parent alpha-amylase. Thus, in one embodiment, the alpha-amylase variant has improved performance, in particular improved wash performance in laundry and/or dish wash, compared to the polypeptide of the parent alpha-amylase.

Thus, in one aspect, the present invention relates to an alpha-amylase variant, comprising a substitution at one or more positions corresponding to positions 109, 51, 201, 269, 294, 297, 298, 193, and 314 of the polypeptide according to SEQ ID NO:3, wherein the variant has alpha-amylase activity, and wherein said parent alpha-amylase has at least 89%, such as at least 90%, such as at least 91%, such as at least 92%, such as at least 93%, such as at least 94%, such as at least 95%, sequence identity to the polypeptide of SEQ ID NOs: 3 or 13.

The term "variant" as used herein, refers to a polypeptide which has been altered in specific amino acid positions, and thus, comprises a different amino acid sequence than the parent polypeptide.

The terms "parent polypeptide" or "parent alpha-amylase" as used herein, refers to a polypeptide which has at least 89%, at least 90%, at least 91%, at least 92%, at least 93%, at least 94%, at least 95%, at least 96%, at least 97%, at least 98%, at least 99% or 100% sequence identity to the polypeptide of SEQ ID NOs: 3 or 13. Thus, in one embodiment, the parent polypeptide has at least 89%, at least 90%, at least 91%, at least 92%, at least 93%, at least 94%, at least 95%, at least 96%, at least 97%, at least 98%, at least 99% or 100% sequence identity to the polypeptide of SEQ ID NO: 3. Thus, in one embodiment, the parent polypeptide has at least 89%, at least 90%, at least 91%, at least 92%, at least 93%, at least 94%, at least 95%, at least 96%, at least 97%, at least 98%, at least 99% or 100% sequence identity to the polypeptide of SEQ ID NO: 13. The parent polypeptide according to SEQ ID NOs: 3 or 13 may comprise alterations in positions which are not positions 51, 109, 193, 201, 269, 294, 298, and 314 when referring to SEQ ID NO: 3. I.e. when the parent alpha-amylase is a polypeptide having at least 89% sequence identity to SEQ ID NO: 13, and the numbering is according to SEQ ID NO: 13, the parent alpha-amylase may comprise alterations in positions which are not positions 51, 109, 195, 203, 271, 296, and 316. In one embodiment, the parent polypeptide is a polypeptide which in at least the amino acid positions 51, 109, 193, 201, 269, 294, 297, 298, and 314 when referring to SEQ ID NO: 3 has the amino acids Q, M, N, G, T, M, Q, A, and N, respectively. Accordingly, the amino acid positions of a parent polypeptide as used in relation to the present invention at least have the following amino acids; Q51, M109, N193, G201, T269, M294, Q297, A298, and N314. In a further embodiment, the parent polypeptide has at least 89%, at least 90%, at least 91%, at least 92%, at least 93%, at least 94%, at least 95%, at least 96%, at least 97%, at least 98%, at least 99% or 100% sequence identity to the polypeptide of SEQ ID NOs: 3 or 13 but wherein the amino acids in positions 51, 109, 193, 201, 269, 294, 297, 298, and 314 when referring to SEQ ID NO: 3 are the amino acids Q, M, N, G, T, M, Q, A, and N, respectively.

The parent polypeptide of the present invention is not limited to the polypeptide of SEQ ID NO: 3, but may also refer to other known alpha-amylase sequences, such as the sequence set forth in SEQ ID NO: 6, 7, 8, 9, 10, 11, 12, or 13. The skilled person knows how to align any of SEQ ID NOs: 6, 7, 8, 9, 10, 11, 12, or 13 with SEQ ID NO: 3 as described herein in order to determine which position the variant according to the present invention corresponds to in the aligned sequences.

The term "alpha-amylase" means, as described herein, an enzyme that has alpha-amylase activity (EC 3.2.1.1) which facilitates the removal of starch-containing stains such as those from pasta and potato. The alpha-amylase variants of the present invention typically consist of three domains (A, B, and C) with the catalytic site between the A and B domains.

The term "polypeptide" as used herein, refers to a sequence of amino acids which are connected to one another via peptide (amide) bonds, i.e. a long, continuous, and unbranched peptide chain. It is within the knowledge of the skilled person to define a polypeptide.

The term "having alpha-amylase activity" as used herein, refers to a polypeptide which can be shown to be active in an assay testing for alpha-amylase activity. Such as assay may be the Amylazyme activity assay. Thus, in one embodiment, the alpha-amylase activity is determined by a method comprising the steps of; (i) incubating the polypeptide with a dyed amylose substrate, and (ii) measuring the amylase activity of the polypeptide. In another embodiment, the alpha-amylase activity is determined by a method comprising the steps of; (i) adding to a composition comprising AZCL-amylose, lactose, magnesium stearate and a blue dye covalently bound in the composition, the polypeptide to be tested; and (ii) measuring the concentration of dye released upon degradation at 590 nm. The term "polypeptide of the invention" or merely "polypeptide" are to be understood as a "polypeptide having alpha-amylase activity according to the invention" unless otherwise clearly stated.

The variants according to the present invention have an improved performance, such as wash performance, as when compared to the parent alpha-amylase. Additionally, the variants may also have an improved stability, such as storage stability, when compared to the parent alpha-amylase In particular embodiments, the variants have similar stability as compared to the parent alpha-amylase, but an improved performance.

In one embodiment, the variant is a variant of a parent alpha-amylase selected from the group consisting of:
 a. a polypeptide having at least 89%, sequence identity to the polypeptide of SEQ ID NOs: 3 or 13;
 b. a polypeptide encoded by a polynucleotide that hybridizes under low stringency conditions with (i) the mature polynucleotide coding sequence of SEQ ID NO: 1, or (ii) the full-length complement of (i);
 c. a polypeptide encoded by a polynucleotide having at least 89% sequence identity to the mature polynucleotide coding sequence of SEQ ID NO:1; and
 d. a fragment of the polypeptide of SEQ ID NOs: 3 or 13, which has alpha-amylase activity.

The term "sequence identity" as used herein, has the same meaning and purpose as stated elsewhere herein. Furthermore, it is within the knowledge of the skilled person to determine the sequence identity of a polypeptide as well as a polynucleotide.

The term "hybridizes" as used herein, refers to the process of establishing a non-covalent, sequence-specific interaction between two or more complementary strands of nucleic acids into a complex. The skilled person would know how to recognize hybridization of complementary sequences.

The term "low stringency conditions" as used herein, has the same meaning and purpose as elsewhere described herein.

The term "full-length" as used herein, refers to the complete sequence of sequence of a polypeptide sequence provided in any of the sequences submitted herewith in the sequence listing. Other full-length sequences may also be contemplated to be part of such definition. It is within the knowledge of the skilled person to determine a full-length of e.g. a nucleotide sequence.

In one embodiment, the parent alpha-amylase has at least 67%, such as at least 70%, at least 75%, at least 80%, at least 85%, at least 90%, at least 95%, at least 96%, at least 97%, at least 98%, at least 99% or 100% sequence identity to the polynucleotide of SEQ ID NO:1.

In another embodiment, the parent alpha-amylase is encoded by a polynucleotide that hybridizes under low stringency conditions, medium stringency conditions, medium-high stringency conditions, high stringency conditions, or very high stringency conditions with (i) the polynucleotide coding sequence of SEQ ID NO: 1 or (ii) the full-length complement of (i).

In yet another embodiment, the parent alpha-amylase is encoded by a polynucleotide having at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 3.

In yet another embodiment, the parent alpha-amylase is encoded by a polynucleotide having at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 13.

In yet another embodiment, the parent alpha-amylase comprises or consists of the mature polynucleotide of SEQ ID NO: 1.

In one embodiment, the parent alpha-amylase is a fragment of the polypeptide of SEQ ID NO: 3, wherein the fragment has alpha-amylase activity.

In one embodiment, the total number of alterations in the parent alpha-amylase is between 3 and 40, preferably between 3 and 30, more preferably between 3 and 20, even more preferably between 3 and 15, most preferably between 3 and 10 alterations, such as substitutions. In one embodiment, the total number of alterations in the parent alpha-amylase is 2, 3, 4, 5, 6, 7, 8, 9, 10, 11, 12, 13, 14, 15, 16, 17, 18, 19, or 20 alterations, such as substitutions.

Variants

In one aspect of the invention, the variant according to the invention has a sequence identity of at least 67%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the polypeptide according to SEQ ID NOs: 3 or 13.

In one embodiment, the variant has a sequence identity of at least 67%, such as at least 70%, at least 75%, at least 80%, at least 85%, at least 90%, at least 95%, at least 96%, at least 97%, at least 98%, or at least 99%, but less than 100% sequence identity to the polypeptide according to SEQ ID NOs: 3 or 13.

In one embodiment, the variant consists of 400 to 490, such as 410 to 490, such as 420 to 490, such as 440 to 486 amino acids.

In one embodiment, the number of substitutions in the variants of the present invention is 1 to 40, e.g. 1 to 30, e.g. 1 to 20, e.g., 1 to 10 and 1 to 5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 substitutions. In a particular embodiment, the variant according to any one of the preceding claims, wherein the number of substitutions is 1 to 20, e.g., 1 to 10 and 1 to 5, such as 1, 2, 3, 4, 5, 6, 7, 8, 9, 10, 11, 12, 13, 14, 15, 16, 17, 18, 19, or 20 alterations.

In a further embodiment, the variant of the present invention comprises further alterations. Such alterations may be an insertion or a deletion. An insertion means adding one or more (e.g. several) amino acids, e.g. 1 to 5 amino acids, adjacent to the amino acid occupying a position. A deletion means deleting one or more (e.g. several) amino acids, e.g. 1 to 5 amino acids, in a polypeptide. The term "alteration" has the same meaning and purpose as described elsewhere herein.

In one embodiment, the alpha-amylase variant has improved performance, in particular improved wash performance in laundry and/or dish washing, compared to the polypeptide of SEQ ID NO:2 or the polypeptide of SEQ ID NOs: 3 or 13.

Thus, in one embodiment, the variant comprises a substitution at one position corresponding to any one of positions 109, 51, 201, 269, 294, 297, 298, 193, and 314 of the polypeptide of SEQ ID NO:3.

In one embodiment, the parent alpha-amylase is the alpha-amylase having the amino acid sequence of SEQ ID NO:2 or the amino acid sequence of SEQ ID NOs: 3 or 13.

In one embodiment, the variant comprises a substitution at a position corresponding to position 51 of SEQ ID NO:3. In one embodiment, the substitution is Q51X, wherein X may be any amino acid selected from the group consisting of: T, A, R, N, D, C, E, G, H, I, L, K, M, F, P, S, W, Y, and V. Thus, in one embodiment, the substitution is Q51T, Q51A, Q51R, Q51N, Q51D, Q51C, Q51E, Q51E, Q51H, Q51I, Q51L, Q51L, Q51K, Q51M, Q51F, Q51P, Q51S, Q51W, Q51Y, or Q51V. In a particular embodiment, the substitution is Q51T. Thus, in one embodiment, the variant comprises or consists of the substitution Q51T of the polypeptide of SEQ ID NO:3. In another particular embodiment, the substitution is Q51D. Thus, in one embodiment, the variant comprises or consists of the substitution Q51D of the polypeptide of SEQ ID NO:3. Thus, in one embodiment, the variant comprises or consists of the substitution Q51T of the polypeptide of SEQ ID NO:13. In another particular embodiment, the substitution is Q51D. Thus, in one embodiment, the variant comprises or consists of the substitution Q51D of the polypeptide of SEQ ID NO:13.

In one embodiment, the variant comprises a substitution at a position corresponding to position 109 of SEQ ID NO:3. In one embodiment, the substitution is M109X, wherein X may be any amino acid selected from the group consisting of: G, A, R, N, D, C, E, Q, H, I, L, K, F, P, S, T, W, Y, and V. Thus, in one embodiment, the substitution is M109G, M109A, M109R, M109N, M109D, M109C, M109E, M109Q, M109H, M109I, M109L, M109K, M109F, M109P, M109S, M109T, M109Y, or M109V. In a particular embodiment, the substitution is M109G. Thus, in one embodiment, the variant comprises or consists of the substitution M109G of the polypeptide of SEQ ID NO:3. In another particular embodiment, the substitution is M109A. Thus, in one embodiment, the variant comprises or consists of the substitution M109A of the polypeptide of SEQ ID NO:3. In another particular embodiment, the substitution is M109G. Thus, in one embodiment, the variant comprises or consists of the substitution M109H. Thus, in one embodiment, the variant comprises or consists of the substitution M109H of the polypeptide of SEQ ID NO:3. In another particular embodiment, the substitution is M109L. Thus, in one embodiment, the variant comprises or consists of the substitution M109L of the polypeptide of SEQ ID NO:3. Thus, in one embodiment, the variant comprises or consists of the substitution M109G of the polypeptide of SEQ ID NO:13. In another particular embodiment, the substitution is M109A. Thus, in one embodiment, the variant comprises or consists of the substitution M109A of the polypeptide of SEQ ID NO:13. In another particular embodiment, the substitution is M109G. Thus, in one embodiment, the variant comprises or consists of the substitution M109H. Thus, in one embodiment, the variant comprises or consists of the substitution M109H of the polypeptide of SEQ ID NO:13. In another particular embodiment, the substitution is M109L. Thus, in one embodiment, the variant comprises or consists of the substitution M109L of the polypeptide of SEQ ID NO:13.

In one embodiment, the variant comprises a substitution at a position corresponding to position 193 of SEQ ID NO:3. In one embodiment, the substitution is N193X, wherein X may be any amino acid selected from the group consisting of: F, A, R, D, C, E, Q, G, H, I, L, K, M, P, S, T, W, Y, and V. Thus, in one embodiment, the substitution is N193F, N193A, N193R, N193D, N193C, N193E, N193Q, N193G, N193H, N193I, N193L, N193K, N193M, N193P, N193S, N193T, N193W, N193Y, or N193V. In a particular embodiment, the substitution is N193F. Thus, in one embodiment, the variant comprises or consists of the substitution N193F of the polypeptide of SEQ ID NO:3. Thus, in one embodiment, the variant comprises or consists of the substitution N193F of the polypeptide of SEQ ID NO:13.

In one embodiment, the variant comprises a substitution at a position corresponding to position 201 of SEQ ID NO:3. In one embodiment, the substitution is G201X, wherein X may be any amino acid selected from the group consisting of: Y, A, R, D, C, E, Q, H, I, L, K, M, N, P, S, T, W, Y, and V. Thus, in one embodiment, the substitution is G201Y, G201A, G201R, G201D, G201C, G201E, G201Q, G201H, G201I, G201L, G201K, G201M, G201N, G201P, G201S, G201T, G201W, G201Y, or G201V. In a particular embodiment, the substitution is G201Y. Thus, in one embodiment, the variant comprises or consists of the substitution G201Y of the polypeptide of SEQ ID NO:3. In another particular embodiment, the substitution is G201 F. Thus, in one embodiment, the variant comprises or consists of the substitution G201F of the polypeptide of SEQ ID NO:3. Thus, in one embodiment, the variant comprises or consists of the substitution G201Y of the polypeptide of SEQ ID NO:13. In another particular embodiment, the substitution is G201F. Thus, in one embodiment, the variant comprises or consists of the substitution G201F of the polypeptide of SEQ ID NO:13.

In one embodiment, the variant comprises a substitution at a position corresponding to position 269 of SEQ ID NO:3. In one embodiment, the substitution is T269X, wherein X may be any amino acid selected from the group consisting of: N, A, R, D, C, E, G, F, Q, H, I, L, K, M, P, S, W, Y and V. Thus, in one embodiment, the substitution is T269N, T269A, T269R, T269D, T269C, T269E, T269G, T269F, T269Q, T269H, T269I, T269L, T269K, T269M, T269P, T269S, T269W, T269Y, or T269V. In a particular embodiment, the substitution is T269N. Thus, in one embodiment, the variant comprises or consists of the substitution T269N of the polypeptide of SEQ ID NO:3. In another particular embodiment, the substitution is T269Y. Thus, in one embodiment, the variant comprises or consists of the substitution T269Y of the polypeptide of SEQ ID NO:3. In another particular embodiment, the substitution is T269G. Thus, in one embodiment, the variant comprises or consists of the substitution T269G of the polypeptide of SEQ ID NO:3. Thus, in one embodiment, the variant comprises or consists of the substitution T269N of the polypeptide of SEQ ID NO:13. In another particular embodiment, the substitution is T269Y. Thus, in one embodiment, the variant comprises or consists of the substitution T269Y of the polypeptide of SEQ ID NO:13. In another particular embodiment, the substitution is T269G. Thus, in one embodiment, the variant comprises or consists of the substitution T269G of the polypeptide of SEQ ID NO:13.

In one embodiment, the variant comprises a substitution at a position corresponding to position 294 of SEQ ID NO:3. In one embodiment, the substitution is M294X, wherein X may be any amino acid selected from the group consisting of: Y, A, R, D, C, E, Q, G, F, H, I, L, K, N, P, S, T, W, and V. Thus, in one embodiment, the substitution is M294G, M294A, M294R, M294N, M294D, M294C, M294E, M294Q, M294H, M294I, M294L, M294K, M294F, M294P, M294S, M294T, M294Y, or M294V. In a particular embodiment, the substitution is M294Y. Thus, in one embodiment, the variant comprises or consists of the substitution M294Y of the polypeptide of SEQ ID NO:3. In another particular embodiment, the substitution is M294N. Thus, in one embodiment, the variant comprises or consists of the substitution M294N of the polypeptide of SEQ ID NO:3. Thus, in one embodiment, the variant comprises or consists of the substitution M294Y of the polypeptide of SEQ ID NO:13. In another particular embodiment, the substitution is M294N. Thus, in one embodiment, the variant comprises or consists of the substitution M294N of the polypeptide of SEQ ID NO:13.

In one embodiment, the variant comprises a substitution at a position corresponding to position 297 of SEQ ID NO:3. In one embodiment, the substitution is Q297X, wherein X may be any amino acid selected from the group consisting of: Y, A, R, N, D, C, E, G, H, I, L, K, M, F, P, S, T, W, and V. Thus, in one embodiment, the substitution is Q297T, Q297A, Q297R, Q297N, Q297D, Q297C, Q297E, Q297E, Q297H, Q297I, Q297L, Q297L, Q297K, Q297M, Q297F, Q297P, Q297S, Q297W, Q297Y, or Q297V. In a particular embodiment, the substitution is Q297Y. Thus, in one embodiment, the variant comprises or consists of the substitution Q297Y of the polypeptide of SEQ ID NO:3. Thus, in one embodiment, the variant comprises or consists of the substitution Q297Y of the polypeptide of SEQ ID NO:13.

In one embodiment, the variant comprises a substitution at a position corresponding to position 298 of SEQ ID NO:3. In one embodiment, the substitution is A298X, wherein X may be any amino acid selected from the group consisting of: N, R, D, C, E, Q, G, H, I, L, K, M, F, P, S, T, W, Y, and V. Thus, in one embodiment, the substitution is A298N, A298R, A298D, A298C, A298E, A298Q, A298G, A298H, A298I, A298L, A298K, A298M, A298F, A298P, A298S, A298T, A298W, A298Y, or A298V. In a particular embodiment, the substitution is A298N. Thus, in one embodiment, the variant comprises or consists of the substitution A298N of the polypeptide of SEQ ID NO:3. Thus, in one embodiment, the variant comprises or consists of the substitution A298N of the polypeptide of SEQ ID NO:13.

In one embodiment, the variant comprises a substitution at a position corresponding to position 314 of SEQ ID NO:3. In one embodiment, the substitution is N314X, wherein X may be any amino acid selected from the group consisting of: G, A, R, D, C, E, Q, H, I, L, K, M, F, P S, T, W, Y, and V. Thus, in one embodiment, the substitution is N314F, N314A, N314R, N314D, N314C, N314E, N314Q, N314G, N314H, N314I, N314L, N314K, N314M, N314P, N314S, N314T, N314W, N314Y, or N314V. In a particular embodiment, the substitution is N314G. Thus, in one embodiment, the variant comprises or consists of the substitution N314G of the polypeptide of SEQ ID NO:3. Thus, in one embodiment, the variant comprises or consists of the substitution N314G of the polypeptide of SEQ ID NO:13.

In an embodiment, the alpha-amylase variant comprises or consists of one or more of the substitutions in Table 1, wherein each position corresponds to the corresponding position of the polypeptide of SEQ ID NO:3.

TABLE 1

| Alpha-amylase variants |
| --- |
| Q51T |
| M109G |
| N193F |
| G201Y |
| T269N |
| M294Y |
| Q297Y |
| A298N |
| N314G |

In a preferred embodiment, the variant is a polypeptide having said substitutions according to the invention and having an amino acid sequence which is at least 67% identical to SEQ ID NO: 3. Thus, in one embodiment, the alpha-amylase variant comprises or consists of the substitution Q51T, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution M109G, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution N193F, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution G201Y, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution T269N, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution M294Y, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution Q297Y, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution A298N, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In one embodiment, the alpha-amylase variant comprises or consists of the substitution N314G, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

Accordingly, in one embodiment, the substitution is selected from the list consisting of;
  i. Q51T, Q51A, Q51R, Q51N, Q51D, Q51C, Q51E, Q51G, Q51H, Q51I , Q51L, Q51K, Q51M, Q51F, Q51P, Q51S, Q51W, Q51Y, or Q51V;
  ii. M109G, M109A, M109H, M109L, M109R, M109N, M109D, M109C, M109E, M109Q, M109I, M109K, M109F, M109P, M109S, M109T, M109W, M109Y, or M109V;
  iii. N193F, N193A, N193R, N193D, N193C, N915E, N193Q, N193G, N193H, N193I, N193L, N193K, N193M, N193P, N193S, N193T, N193W, N193Y, or N193V;
  iv. G201Y, G201A, G201R, G201D, G201C, G201E, G201Q, G201H, G201I, G201L, G201K, G201M, G201N, G201P, G201S, G201T, G201W, G201Y, or G201V;
  v. T269N, T269Y, T269G, T269A, T269R, T269D, T269C, T269E, T269F, T269Q, T269H, T269I, T269L, T269K, T269M, T269P, T269S, T269W, or T269V;
  vi. M294Y, M294N, M294A, M294R, M294D, M294C, M294E, M294Q, M294G, M294F, M294H, M294I, M294L, M294K, M294P, M294S, M294T, M294W, or M294V;
  vii. Q297Y, Q297A, Q297R, Q297N, Q297D, Q297C, Q297E, Q297G, Q297H, Q297I, Q297L, Q297K, Q297M, Q297F, Q297P, Q297S, Q297T, Q297W, or Q297V;
  viii. A298N, A298R, A298D, A298C, A298E, A298Q, A298G, A298H, A298I, A298L, A298K, A298M, A298F, A298P, A298S, A298T, A298W, A298Y, or A298V; or
  ix. N314G, N314A, N314R, N314D, N314C, N314E, N314Q, N314H, N314I, N314L, N314K, N314M, N314F, N314P, N314S, N314T, N314W, N314Y, or N314V, wherein each position corresponds to the corresponding position in the polypeptide of SEQ ID NO:3.

In another aspect, the present invention relates to a variant which comprises a substitution at two positions corresponding to any one of positions 109, 51, 201, 269, 294, 297, 298, 193, and 314 of the polypeptide of SEQ ID NO: 3. The substitution in each amino acid position is contemplated to be any of those described elsewhere herein.

Accordingly, the invention also relates to alpha-amylase variants comprising substitutions in two positions corresponding to those pairwise listed in Table 2, wherein each position corresponds to the corresponding position of the mature polypeptide of SEQ ID NO:2 or the polypeptide of SEQ ID NOs: 3 or 13.

TABLE 2

| Alpha-amylase variants | | |
|---|---|---|
| Q51 + M109 | Q51 + N193 | Q51 + G201 |
| Q51 + T269 | Q51 + M294 | Q51 + Q297 |
| Q51 + A298 | Q51 + N314 | M109 + N193 |
| M109 + G201 | M109 + T269 | M109 + M294 |
| M109 + Q297 | M109 + A298 | M109 + N314 |
| N193 + G201 | N193 + T269 | N193 + M294 |
| N193 + Q297 | N193 + A298 | N193 + N314 |
| T269 + M294 | T269 + Q297 | T269 + A298 |
| T269 + N314 | M294 + Q297 | M294 + A298 |
| M294 + N314 | Q297 + A298 | Q297 + N314 |
| A298 + N314 | | |

Combining two positions may further enhance the improved performance of the variants. Thus, in one embodiment, the alpha-amylase variants of the present invention comprises the specific pairwise amino acid substitutions listed in Table 3, wherein each position corresponds to the position of the mature polypeptide of SEQ ID NO: 2 or the polypeptide of SEQ ID NO: 3.

TABLE 3

| Alpha-amylase variants | | |
|---|---|---|
| Q51T + M109G | Q51T + N193F | Q51T + G201Y |
| Q51T + T269N | Q51T + M294Y | Q51T + Q297Y |
| Q51T + A298N | Q51T + N314G | M109G + N193F |
| M109G + G201Y | M109G + T269N | M109G + M294Y |
| M109G + Q297Y | M109G + A298N | M109G + N314G |
| N193F + G201Y | N193F + T269N | N193F + M294Y |
| N193F + Q297Y | N193F + A298N | N193F + N314G |
| T269N + M294Y | T269N + Q297Y | T269N + A298N |
| T269N + N314G | M294Y + Q297Y | M294Y + A298N |
| M294Y + N314G | Q297Y + A298N | Q297Y + N314G |
| A298N + N314G | | |

In a particular embodiment, the variant comprises two of the substitutions selected from the list consisting of Q51T, Q51D, M109G, M109G, M109H, M109L, N193F, G201Y, G201F, T269N, T269Y, T269G, M294Y, M294N, Q297Y, A298N, and N314G, wherein each position corresponds to the corresponding position of the polypeptide of SEQ ID NO:3.

In another embodiment, the variant comprises or consists of substitutions at positions corresponding to positions 51 and 109, such as those described above, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 51 and 193, such as those described above, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 51 and 269, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 51 and 294, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 51 and 297, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 51 and 298, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 51 and 314, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 109 and 193, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 109 and 269, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 109 and 294, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 109 and 297, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 109 and 298, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 109 and 314, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 193 and 269, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 193 and 294, such as those described above wherein the position corresponds to the corresponding positions of SEQ ID NO:

3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 193 and 297, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 193 and 298, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 193 and 314, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 269 and 294, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 269 and 297, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 269 and 298, such as those described above wherein the position corresponds to the corresponding positions of SEQ ID NO:3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 269 and 314, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 294 and 297, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 294 and 298, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 294 and 314, such as those described above wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 297 and 298, such as those described above, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 297 and 314, such as those described above, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the variant comprises or consists of substitutions at positions corresponding to positions 298 and 314, such as those described above, wherein the position corresponds to the corresponding positions of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In another embodiment, the alpha-amylase variants comprises amino acid substitutions in three positions corresponding to those listed in Table 4, wherein each position corresponds to the corresponding positions of the polypeptide of SEQ ID NO:3. Thus, in one embodiment, the alpha-amylase variant comprises or consists of substitutions in three positions each selected from the list consisting of 51, 109, 193, 201, 269, 294, 297, 298, and 314, wherein each position corresponds to the corresponding positions of the polypeptide of SEQ ID NO:3. In one embodiment, the alpha-amylase variant comprises or consists of substitutions in three positions each selected from the list consisting of 51, 109, 193, 201, 269, 294, 297, 298, and 314, wherein each position corresponds to the corresponding positions of the polypeptide of SEQ ID NO:3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In a particular embodiment, the variant comprises a substitution at each position corresponding to positions;
(i) 51 and 109;
(ii) 109 and 201;
(iii) 269 and 294; or
(iv) 294 and 297;
wherein each position corresponds to the corresponding positions in the polypeptide of SEQ ID NO 3.

In one particular embodiment, the variant comprises the substitutions;
(i) Q51T and M109G;
(ii) M109G and G201Y;
(iii) M109G and G201F
(iv) T269N and M294Y;
(v) T269N and M294F;
(vi) T269Y and M294N; or
(vii) M294Y and Q297Y;
wherein each position corresponds to the corresponding positions in the polypeptide of SEQ ID NO: 3.

In one embodiment, the variant comprises a substitution at three positions corresponding to any of positions 109, 51, 201, 269, 294, 297, 298, 193, and 314 of the polypeptide of SEQ ID NO:3. In one embodiment, the variant comprises a substitution at three positions corresponding to any of positions 109, 51, 203, 271, 296, 299, 300, 195, and 316 of the polypeptide of SEQ ID NO:13.

TABLE 4

| Alpha-amylase variants | | |
|---|---|---|
| Q51 + M109 + N193 | Q51 + M109 + G201 | Q51 + M109 + T269 |
| Q51 + M109 + M294 | Q51 + M109 + Q297 | Q51 + M109 + A298 |
| Q51 + M109 + N314 | Q51 + N193 + G201 | Q51 + N193 + T269 |
| Q51 + N193 + M294 | Q51 + N193 + Q297 | Q51 + N193 + A298 |
| Q51 + N193 + N314 | Q51 + G201 + T269 | Q51 + G201 + M294 |

TABLE 4-continued

| Alpha-amylase variants | | |
|---|---|---|
| Q51 + G201 + Q297 | Q51 + G201 + A298 | Q51 + G201 + N314 |
| Q51 + T269 + M294 | Q51 + T269 + Q297 | Q51 + T269 + A298 |
| Q51 + T269 + N314 | Q51 + M294 + Q297 | Q51 + M294 + A298 |
| Q51 + M294 + N314 | Q51 + Q297 + A298 | Q51 + Q297 + N314 |
| Q51 + A298 + N314 | M109 + N193 + G201 | M109 + N193 + T269 |
| M109 + N193 + M294 | M109 + N193 + Q297 | M109 + N193 + A298 |
| M109 + N193 + N314 | M109 + G201 + T269 | M109 + G201 + M294 |
| M109 + G201 + Q297 | M109 + G201 + A298 | M109 + G201 + N314 |
| M109 + T269 + M294 | M109 + T269 + Q297 | M109 + T269 + A298 |
| M109 + T269 + N314 | M109 + M294 + Q297 | M109 + M294 + A298 |
| M109 + M294 + N314 | M109 + Q297 + A298 | M109 + Q297 + N314 |
| M109 + A298 + N314 | N193 + G201 + T269 | N193 + G201 + M294 |
| N193 + G201 + Q297 | N193 + G201 + A298 | N193 + G201 + N314 |
| N193 + T269 + M294 | N193 + T269 + Q297 | N193 + T269 + A298 |
| N193 + T269 + N314 | N193 + M294 + Q297 | N193 + M294 + A298 |
| N193 + M294 + N314 | N193 + Q297 + A298 | N193 + Q297 + N314 |
| N193 + A298 + N314 | G201 + T269 + M294 | G201 + T269 + Q297 |
| G201 + T269 + A298 | G201 + T269 + N314 | G201 + M294 + Q297 |
| G201 + M294 + A298 | G201 + M294 + N314 | G201 + Q297 + A298 |
| G201 + Q297 + N314 | G201 + A298 + N314 | T269 + M294 + Q297 |
| T269 + M294 + A298 | T269 + M294 + N314 | T269 + Q297 + A298 |
| T269 + Q297 + N314 | T269 + A298 + N314 | M294 + Q297 + A298 |
| M294 + Q297 + N314 | M294 + A298 + N314 | Q297 + A298 + N314 |

In one embodiment, the alpha-amylase variants of the present invention comprise or consist of the amino acid substitutions listed in Table 5. Thus, in one embodiment, the alpha-amylase variant comprises or consists of three of the amino acid substitutions individually selected from the list consisting of Q51T, Q51D, M109G, M109G, M109H, M109L, N193F, G201Y, G201F, T269N, T269Y, T269G, M294Y, M294N, Q297Y, A298N, and N314G, wherein each position corresponds to the corresponding position of SEQ ID NO: 3. In one embodiment, the alpha-amylase variant comprises or consists of three of the amino acid substitutions individually selected from the list consisting of Q51T, Q51D, M109G, M109G, M109H, M109L, N193F, G201Y, G201F, T269N, T269Y, T269G, M294Y, M294N, Q297Y, A298N, and N314G, wherein each position corresponds to the corresponding position of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

TABLE 5

| Alpha-amylase variants | | |
|---|---|---|
| Q51T + M109G + G201Y | Q51D + T269G + M294Y | M109L + G201Y + T269N |
| Q51T + M109G + G201F | Q51D + T269G + M294N | M109L + G201Y + T269Y |
| Q51T + M109G + T269N | Q51D + T269G + Q297Y | M109L + G201Y + T269G |
| Q51T + M109G + T269Y | Q51D + T269G + A298N | M109L + G201Y + M294Y |
| Q51T + M109G + T269G | Q51D + T269G + N314G | M109L + G201Y + M294N |
| Q51T + M109G + M294Y | Q51D + M294Y + Q297Y | M109L + G201Y + Q297Y |
| Q51T + M109G + M294N | Q51D + M294Y + A298N | M109L + G201Y + A298N |
| Q51T + M109G + Q297Y | Q51D + M294Y + N314G | M109L + G201Y + N314G |
| Q51T + M109G + A298N | Q51D + M294N + Q297Y | M109L + G201F + T269N |
| Q51T + M109G + N314G | Q51D + M294N + A298N | M109L + G201F + T269Y |
| Q51T + M109G + N193F | Q51D + M294N + N314G | M109L + G201F + T269G |
| Q51T + M109G + G201Y | Q51D + Q297Y + A298N | M109L + G201F + M294Y |
| Q51T + M109G + G201F | Q51D + Q297Y + N314G | M109L + G201F + M294N |
| Q51T + M109G + T269N | Q51D + A298N + N314G | M109L + G201F + Q297Y |
| Q51T + M109G + T269Y | M109G + N193F + G201Y | M109L + G201F + A298N |
| Q51T + M109G + T269G | M109G + N193F + G201F | M109L + G201F + N314G |
| Q51T + M109G + M294Y | M109G + N193F + T269N | M109L + T269N + M294Y |
| Q51T + M109G + M294N | M109G + N193F + T269Y | M109L + T269N + M294N |
| Q51T + M109G + Q297Y | M109G + N193F + T269G | M109L + T269N + Q297Y |
| Q51T + M109G + A298N | M109G + N193F + M294Y | M109L + T269N + A298N |
| Q51T + M109G + N314G | M109G + N193F + M294N | M109L + T269N + N314G |
| Q51T + M109H + M109L | M109G + N193F + Q297Y | M109L + T269Y + M294Y |

TABLE 5-continued

Alpha-amylase variants

| | | |
|---|---|---|
| Q51T + M109H + N193F | M109G + N193F + A298N | M109L + T269Y + M294N |
| Q51T + M109H + G201Y | M109G + N193F + N314G | M109L + T269Y + Q297Y |
| Q51T + M109H + G201F | M109G + G201Y + T269N | M109L + T269Y + A298N |
| Q51T + M109H + T269N | M109G + G201Y + T269Y | M109L + T269Y + N314G |
| Q51T + M109H + T269Y | M109G + G201Y + T269G | M109L + T269G + M294Y |
| Q51T + M109H + T269G | M109G + G201Y + M294Y | M109L + T269G + M294N |
| Q51T + M109H + M294Y | M109G + G201Y + M294N | M109L + T269G + Q297Y |
| Q51T + M109H + M294N | M109G + G201Y + Q297Y | M109L + T269G + A298N |
| Q51T + M109H + Q297Y | M109G + G201Y + A298N | M109L + T269G + N314G |
| Q51T + M109H + A298N | M109G + G201Y + N314G | M109L + M294Y + Q297Y |
| Q51T + M109H + N314G | M109G + G201F + T269N | M109L + M294Y + A298N |
| Q51T + M109L + N193F | M109G + G201F + T269Y | M109L + M294Y + N314G |
| Q51T + M109L + G201Y | M109G + G201F + T269G | M109L + M294N + Q297Y |
| Q51T + M109L + G201F | M109G + G201F + M294Y | M109L + M294N + A298N |
| Q51T + M109L + T269N | M109G + G201F + M294N | M109L + M294N + N314G |
| Q51T + M109L + T269Y | M109G + G201F + Q297Y | M109L + Q297Y + A298N |
| Q51T + M109L + T269G | M109G + G201F + A298N | M109L + Q297Y + N314G |
| Q51T + M109L + M294Y | M109G + G201F + N314G | M109L + A298N + N314G |
| Q51T + M109L + M294N | M109G + T269N + M294Y | N193F + G201Y + T269N |
| Q51T + M109L + Q297Y | M109G + T269N + M294N | N193F + G201Y + T269Y |
| Q51T + M109L + A298N | M109G + T269N + Q297Y | N193F + G201Y + T269G |
| Q51T + M109L + N314G | M109G + T269N + A298N | N193F + G201Y + M294Y |
| Q51T + N193F + G201Y | M109G + T269N + N314G | N193F + G201Y + M294N |
| Q51T + N193F + G201F | M109G + T269Y + M294Y | N193F + G201Y + Q297Y |
| Q51T + N193F + T269N | M109G + T269Y + M294N | N193F + G201Y + A298N |
| Q51T + N193F + T269Y | M109G + T269Y + Q297Y | N193F + G201Y + N314G |
| Q51T + N193F + T269G | M109G + T269Y + A298N | N193F + G201F + T269N |
| Q51T + N193F + M294Y | M109G + T269Y + N314G | N193F + G201F + T269Y |
| Q51T + N193F + M294N | M109G + T269G + M294Y | N193F + G201F + T269G |
| Q51T + N193F + Q297Y | M109G + T269G + M294N | N193F + G201F + M294Y |
| Q51T + N193F + A298N | M109G + T269G + Q297Y | N193F + G201F + M294N |
| Q51T + N193F + N314G | M109G + T269G + A298N | N193F + G201F + Q297Y |
| Q51T + G201Y + T269N | M109G + T269G + N314G | N193F + G201F + A298N |
| Q51T + G201Y + T269Y | M109G + M294Y + Q297Y | N193F + G201F + N314G |
| Q51T + G201Y + T269G | M109G + M294Y + A298N | N193F + T269N + M294Y |
| Q51T + G201Y + M294Y | M109G + M294Y + N314G | N193F + T269N + M294N |
| Q51T + G201Y + M294N | M109G + M294N + Q297Y | N193F + T269N + Q297Y |
| Q51T + G201Y + Q297Y | M109G + M294N + A298N | N193F + T269N + A298N |
| Q51T + G201Y + A298N | M109G + M294N + N314G | N193F + T269N + N314G |
| Q51T + G201Y + N314G | M109G + Q297Y + A298N | N193F + T269Y + M294Y |
| Q51T + G201F + T269N | M109G + Q297Y + N314G | N193F + T269Y + M294N |
| Q51T + G201F + T269Y | M109G + A298N + N314G | N193F + T269Y + Q297Y |
| Q51T + G201F + T269G | M109G + N193F + G201Y | N193F + T269Y + A298N |
| Q51T + G201F + M294Y | M109G + N193F + G201F | N193F + T269Y + N314G |
| Q51T + G201F + M294N | M109G + N193F + T269N | N193F + T269G + M294Y |
| Q51T + G201F + Q297Y | M109G + N193F + T269Y | N193F + T269G + M294N |
| Q51T + G201F + A298N | M109G + N193F + T269G | N193F + T269G + Q297Y |
| Q51T + G201F + N314G | M109G + N193F + M294Y | N193F + T269G + A298N |
| Q51T + T269N + M294Y | M109G + N193F + M294N | N193F + T269G + N314G |
| Q51T + T269N + M294N | M109G + N193F + Q297Y | N193F + M294Y + Q297Y |
| Q51T + T269N + Q297Y | M109G + N193F + A298N | N193F + M294Y + A298N |
| Q51T + T269N + A298N | M109G + N193F + N314G | N193F + M294Y + N314G |
| Q51T + T269N + N314G | M109G + G201Y + T269N | N193F + M294N + Q297Y |
| Q51T + T269Y + M294Y | M109G + G201Y + T269Y | N193F + M294N + A298N |
| Q51T + T269Y + M294N | M109G + G201Y + T269G | N193F + M294N + N314G |
| Q51T + T269Y + Q297Y | M109G + G201Y + M294Y | N193F + Q297Y + A298N |
| Q51T + T269Y + A298N | M109G + G201Y + M294N | N193F + Q297Y + N314G |
| Q51T + T269Y + N314G | M109G + G201Y + Q297Y | N193F + A298N + N314G |
| Q51T + T269G + M294Y | M109G + G201Y + A298N | G201Y + T269N + M294Y |
| Q51T + T269G + M294N | M109G + G201Y + N314G | G201Y + T269N + M294N |
| Q51T + T269G + Q297Y | M109G + G201F + T269N | G201Y + T269N + Q297Y |
| Q51T + T269G + A298N | M109G + G201F + T269Y | G201Y + T269N + A298N |
| Q51T + T269G + N314G | M109G + G201F + T269G | G201Y + T269N + N314G |
| Q51T + M294Y + Q297Y | M109G + G201F + M294Y | G201Y + T269Y + M294Y |
| Q51T + M294Y + A298N | M109G + G201F + M294N | G201Y + T269Y + M294N |
| Q51T + M294Y + N314G | M109G + G201F + Q297Y | G201Y + T269Y + Q297Y |
| Q51T + M294N + Q297Y | M109G + G201F + A298N | G201Y + T269Y + A298N |
| Q51T + M294N + A298N | M109G + G201F + N314G | G201Y + T269Y + N314G |
| Q51T + M294N + N314G | M109G + T269N + M294Y | G201Y + T269G + M294Y |
| Q51T + Q297Y + A298N | M109G + T269N + M294N | G201Y + T269G + M294N |
| Q51T + Q297Y + N314G | M109G + T269N + Q297Y | G201Y + T269G + Q297Y |
| Q51T + A298N + N314G | M109G + T269N + A298N | G201Y + T269G + A298N |
| Q51D + M109G + N193F | M109G + T269N + N314G | G201Y + T269G + N314G |
| Q51D + M109G + G201Y | M109G + T269Y + T269G | G201Y + M294Y + Q297Y |
| Q51D + M109G + G201F | M109G + T269Y + M294Y | G201Y + M294Y + A298N |
| Q51D + M109G + T269N | M109G + T269Y + M294N | G201Y + M294Y + N314G |
| Q51D + M109G + T269Y | M109G + T269Y + Q297Y | G201Y + M294N + Q297Y |
| Q51D + M109G + T269G | M109G + T269Y + A298N | G201Y + M294N + A298N |

TABLE 5-continued

Alpha-amylase variants

| | | |
|---|---|---|
| Q51D + M109G + M294Y | M109G + T269Y + N314G | G201Y + M294N + N314G |
| Q51D + M109G + M294N | M109G + T269G + M294Y | G201Y + Q297Y + A298N |
| Q51D + M109G + Q297Y | M109G + T269G + M294N | G201Y + Q297Y + N314G |
| Q51D + M109G + A298N | M109G + T269G + Q297Y | G201Y + A298N + N314G |
| Q51D + M109G + N314G | M109G + T269G + A298N | G201F + T269N + M294Y |
| Q51D + M109G + N193F | M109G + T269G + N314G | G201F + T269N + M294N |
| Q51D + M109G + G201Y | M109G + M294Y + Q297Y | G201F + T269N + Q297Y |
| Q51D + M109G + G201F | M109G + M294Y + A298N | G201F + T269N + A298N |
| Q51D + M109G + T269N | M109G + M294Y + N314G | G201F + T269N + N314G |
| Q51D + M109G + T269Y | M109G + M294N + Q297Y | G201F + T269Y + M294Y |
| Q51D + M109G + T269G | M109G + M294N + A298N | G201F + T269Y + M294N |
| Q51D + M109G + M294Y | M109G + M294N + N314G | G201F + T269Y + Q297Y |
| Q51D + M109G + M294N | M109G + Q297Y + A298N | G201F + T269Y + A298N |
| Q51D + M109G + Q297Y | M109G + Q297Y + N314G | G201F + T269Y + N314G |
| Q51D + M109G + A298N | M109G + A298N + N314G | G201F + T269G + M294Y |
| Q51D + M109G + N314G | M109H + N193F + G201Y | G201F + T269G + M294N |
| Q51D + M109H + M109L | M109H + N193F + G201F | G201F + T269G + Q297Y |
| Q51D + M109H + N193F | M109H + N193F + T269N | G201F + T269G + A298N |
| Q51D + M109H + G201Y | M109H + N193F + T269Y | G201F + T269G + N314G |
| Q51D + M109H + G201F | M109H + N193F + T269G | G201F + M294Y + Q297Y |
| Q51D + M109H + T269N | M109H + N193F + M294Y | G201F + M294Y + A298N |
| Q51D + M109H + T269Y | M109H + N193F + M294N | G201F + M294Y + N314G |
| Q51D + M109H + T269G | M109H + N193F + Q297Y | G201F + M294N + Q297Y |
| Q51D + M109H + M294Y | M109H + N193F + A298N | G201F + M294N + A298N |
| Q51D + M109H + M294N | M109H + N193F + N314G | G201F + M294N + N314G |
| Q51D + M109H + Q297Y | M109H + G201Y + T269N | G201F + Q297Y + A298N |
| Q51D + M109H + A298N | M109H + G201Y + T269Y | G201F + Q297Y + N314G |
| Q51D + M109H + N314G | M109H + G201Y + T269G | G201F + A298N + N314G |
| Q51D + M109L + N193F | M109H + G201Y + M294Y | T269N + M294Y + Q297Y |
| Q51D + M109L + G201Y | M109H + G201Y + M294N | T269N + M294Y + A298N |
| Q51D + M109L + G201F | M109H + G201Y + Q297Y | T269N + M294Y + N314G |
| Q51D + M109L + T269N | M109H + G201Y + A298N | T269N + M294N + Q297Y |
| Q51D + M109L + T269Y | M109H + G201Y + N314G | T269N + M294N + A298N |
| Q51D + M109L + T269G | M109H + G201F + T269N | T269N + M294N + N314G |
| Q51D + M109L + M294Y | M109H + G201F + T269Y | T269N + Q297Y + A298N |
| Q51D + M109L + M294N | M109H + G201F + T269G | T269N + Q297Y + N314G |
| Q51D + M109L + Q297Y | M109H + G201F + M294Y | T269N + A298N + N314G |
| Q51D + M109L + A298N | M109H + G201F + M294N | T269Y + M294Y + Q297Y |
| Q51D + M109L + N314G | M109H + G201F + Q297Y | T269Y + M294Y + A298N |
| Q51D + N193F + G201Y | M109H + G201F + A298N | T269Y + M294Y + N314G |
| Q51D + N193F + G201F | M109H + G201F + N314G | T269Y + M294N + Q297Y |
| Q51D + N193F + T269N | M109H + T269N + M294Y | T269Y + M294N + A298N |
| Q51D + N193F + T269Y | M109H + T269N + M294N | T269Y + M294N + N314G |
| Q51D + N193F + T269G | M109H + T269N + Q297Y | T269Y + Q297Y + A298N |
| Q51D + N193F + M294Y | M109H + T269N + A298N | T269Y + Q297Y + N314G |
| Q51D + N193F + M294N | M109H + T269N + N314G | T269Y + A298N + N314G |
| Q51D + N193F + Q297Y | M109H + T269Y + M294Y | T269G + M294Y + Q297Y |
| Q51D + N193F + A298N | M109H + T269Y + M294N | T269G + M294Y + A298N |
| Q51D + N193F + N314G | M109H + T269Y + Q297Y | T269G + M294Y + N314G |
| Q51D + G201Y + T269N | M109H + T269Y + A298N | T269G + M294N + Q297Y |
| Q51D + G201Y + T269Y | M109H + T269Y + N314G | T269G + M294N + A298N |
| Q51D + G201Y + T269G | M109H + T269G + M294Y | T269G + M294N + N314G |
| Q51D + G201Y + M294Y | M109H + T269G + M294N | T269G + Q297Y + A298N |
| Q51D + G201Y + M294N | M109H + T269G + Q297Y | T269G + Q297Y + N314G |
| Q51D + G201Y + Q297Y | M109H + T269G + A298N | T269G + A298N + N314G |
| Q51D + G201Y + A298N | M109H + T269G + N314G | M294Y + Q297Y + A298N |
| Q51D + G201Y + N314G | M109H + M294Y + Q297Y | M294Y + Q297Y + N314G |
| Q51D + G201F + T269N | M109H + M294Y + A298N | M294Y + A298N + N314G |
| Q51D + G201F + T269Y | M109H + M294Y + N314G | M294N + Q297Y + A298N |
| Q51D + G201F + T269G | M109H + M294N + Q297Y | M294N + Q297Y + N314G |
| Q51D + G201F + M294Y | M109H + M294N + A298N | M294N + A298N + N314G |
| Q51D + G201F + M294N | M109H + M294N + N314G | Q297Y + A298N + N314G |
| Q51D + G201F + Q297Y | M109H + Q297Y + A298N | M109L + N193F + M294N |
| Q51D + G201F + A298N | M109H + Q297Y + N314G | M109L + N193F + Q297Y |
| Q51D + G201F + N314G | M109H + A298N + N314G | M109L + N193F + A298N |
| Q51D + T269N + M294Y | M109L + N193F + G201Y | M109L + N193F + N314G |
| Q51D + T269N + M294N | M109L + N193F + G201F | Q51D + T269Y + M294N |
| Q51D + T269N + Q297Y | M109L + N193F + T269N | Q51D + T269Y + Q297Y |
| Q51D + T269N + A298N | M109L + N193F + T269Y | Q51D + T269Y + A298N |
| Q51D + T269N + N314G | M109L + N193F + T269G | Q51D + T269Y + N314G |
| Q51D + T269Y + M294Y | M109L + N193F + M294Y | |

In another embodiment, the alpha-amylase variant of the invention comprises amino acid substitutions in four or five or six or seven or eight of the positions selected form the list consisting of Q51T, M109G, N193F, G201Y, T269N, M294Y, Q297Y, A298N, and N314G, wherein each position corresponds to the corresponding position of SEQ ID NO: 3. In one embodiment, the alpha-amylase variant comprises or consists of amino acid substitutions in four or five or six or seven or eight of the positions individually selected from the list consisting of Q51T, M109G, N193F, G201Y, T269N, M294Y, Q297Y, A298N, and N314G, wherein each position corresponds to the corresponding position of SEQ ID NO: 3, and wherein the alpha-amylase variant is a polypeptide having at least 67%, such as at least 70%, such as at least 75%, such as at least 80%, such as at least 90%, such as at least 95% sequence identity to the amino acid sequence of SEQ ID NOs: 3 or 13.

In a particular embodiment, the variant comprises a substitution at each positions corresponding to positions;
  (i) 51, 109, 193, and 201;
  (ii) 109, 201, 269, and 294;
  (iii) 201, 269, 294 and 297; or
  (iv) 51, 109, 193, 201, 269, 294, 297, 298, and 314;
wherein each position corresponds to the corresponding positions in the polypeptide of SEQ ID NO: 3.

In a particular embodiment, the variant comprises a substitution at each positions corresponding to positions;
  (i) Q51T, M109G, N193F, and G201Y;
  (ii) M109G, G201Y, T269N, and M294Y;
  (iii) G201Y, T269N, M294Y, and Q297Y; or
  (ii) Q51T, M109G, N193F, G201Y, T269N, M294Y, Q297Y, A298N, and N314G;
wherein each position corresponds to the corresponding positions in the polypeptide of SEQ ID NO: 3.

It is contemplated that each alpha-amylase variant herein described may further has an improved performance, such as an improved wash performance in laundry or in automated dish washing, compared to the parent polypeptide of SEQ ID NOs: 3 or 13.

The variants may further comprise one or more additional substitutions at one or more (e.g., several) other positions.

Thus, in one embodiment, the variant further comprises an alteration at positions corresponding to positions:
105L,I,F+206Y; 105L,I+206Y+217I; 105F+206Y+208Y+217V+246V; 105L+206F; 105I+206Y+208Y+217I+246V; 195F+213S+214T; 195F+206Y+208Y+213T+214T+217M,V; 195F+206Y+208F,L+213T+214T+217V; 195F+206Y+213S+214T; 195F+206Y+208Y+213S+214T+217M; 195F+206Y+208F+213T+214T+217M; 195F+206Y+208Y+213T+214T+217Q; 195F+206Y+213G+214T; 195F+206Y+213S; 195F+206Y+208Y+213T+214T+217M; 195F+213S; 195F+206Y+208L+213T+214T+217M; 195F+213G+214T; 206Y,F+208Y+217Q; 206Y+208Y+217I; 206F+208Y+217M; 206Y+208Y; 206Y+217M; 206Y+208Y+213A+217M; 206Y+208Y+217V+246V; 206Y+213G; 206Y+208F+217V; 206N+208Y+217M; 206F+208Y+217V; 206Y+246V; 206Y+217I,V; 206F+208F+217I; 206Y+208L+213S; 206F+217I; 206Y+217I+246I; 206L+217V; 206Y+208F+217H; 206L+208F+217I; 206L+217V+246L; 206F+246V; 208Y+213S+217M; 208Y+213A+217Q; 63I+206Y; 63I+206Y+241V; 63V+206Y; 63V+105L+206Y; 63V+206Y+217I; 63V+105F+206Y+208F+217I; 63V+206Y+246V; 63V+206F; 63V+206L+217V; 63V+105F+206Y; 63V+206Y+241V+246L; 195F+206Y+208Y+214T+217V; 186E+195F+206Y; 195F+206Y+208Y+213T+217V; 186E+195F+202T+206Y+209S; 63I+195F+206Y+210S; 195F+206Y+213P+214T; 195F+206Y+208Y+213T+214T+217I; 186E+195F+206Y+210S; 195F+213P; 186E+195F+202T+206Y+210S; 195F+206H; 195F+208Y+213T+214T+217V; 206Y+208Y+213T+214T+217V; 195F+206Y+217V; 195F+206Y+208Y+213S+214T; 195F+206Y+208Y; 195F+213I+214P; 195F+206Y+208Y+213T+214T; 195F+206Y; 206Y+213S; 182P+186E; 182S+186E; 182V+186K; 179L+186H+190P; 179L+186K,R,S+190P; 179L+190P; 179L+182C+186K+190P; 179L+182P+186S,V+190P; 179L+182S+186Q+190P; 173F+174Q; 173Y+174S; 172K+173Y+174E; 193A,D,N,S+195F; 213A+214Q; 213P+214L; 213S+214R; 48V+60V; 213G+214T; 213I+214P; 213N+214I; 213N+214Q; and 213P,S+214T; wherein numbering is according to SEQ ID NO:11.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one embodiment, the variant comprises a pairwise deletion selected from the list consisting of: 181 and 182; 181 and 183; 181 and 184; 182 and 183; 182 and 184; and 183 and 184; wherein the positions correspond to the positions of SEQ ID NO: 13.

The term "pairwise deletion" as used herein, refers to a double deletion of two amino acids in close proximity to one another. In close proximity to one another may be two amino acids positioned within five amino acids, such as within four, such as within three, and such as two, distance from one another in an amino acid sequence. The amino acids may also be positioned adjacent to one another.

In a preferred embodiment, the polypeptide has the alterations according to the invention and has an amino acid sequence which is at least 67% identical to SEQ ID NO: 13. Thus, in one embodiment, the polypeptide comprises or consists of the pairwise deletion of amino acids selected from the group consisting of: (a) 181 and 183; (b) 181 and 184; (c) 182 and 183; (d) 182 and 184; and (e) 183 and 184, wherein the positions correspond to the corresponding positions of SEQ ID NO: 13, and wherein the polypeptide has at least 67%, such as at least 70%, such as at least 75%, such as at least 80%, such as at least 90%, such as at least 95% sequence identity to the amino acid sequence of SEQ ID NO: 13.

In one embodiment, the variant of the invention has an improved stability in detergent compositions relative to the parent alpha-amylase of SEQ ID NOs: 3 or 13.

The term "improved stability" as used herein, refers to when the stability, such as the storage stability, of a polypeptide has been enhanced. In particular, it is well-known within the art that polypeptides degrade over time. Thus, an improvement of the stability means that the time before a polypeptide is degraded, in particular the time until the activity of the polypeptide is lost due to degradation, is extended. Accordingly, it is contemplated that an improved stability of the polypeptides of the present invention maintains the activity longer than for, e.g., a parent polypeptide.

The term "detergent composition" as used herein, refers to the definition elsewhere described herein.

In a further embodiment, the improved stability is improved storage stability.

In an embodiment, the improved stability is determined by a method comprising the steps of;
a) incubating an alpha-amylase variant sample and a parent alpha-amylase sample, respectively, in a model detergent composition, such as Model A, Model J, Model T, or Model X, for a period of time;
b) measuring the activity of the variant alpha-amylase and the parent alpha-amylase, respectively; and
c) calculating the residual activity of the samples.

In a further embodiment, the improved stability is determined by a method comprising the steps of;
a) incubating an alpha-amylase variant sample and a parent alpha-amylase sample, respectively, in a model detergent composition, such as Model A, Model J, Model T, or Model X, at 40° C. to 60° C. for 2 to 168 hrs;
b) measuring the activity of the variant alpha-amylase and the parent alpha-amylase, respectively; and
c) calculating the residual activity of the samples as the average of activity in the samples relative to the average of the activity to frozen control samples.

another embodiment, the variant of the invention has an improved performance in detergent compositions relative to the parent alpha-amylase of SEQ ID NOs: 3 or 13.

In a further embodiment, the improved performance is improved wash performance.

The term "improved performance" as used herein, refers to when the performance, such as the wash performance, has been enhanced. Performance may be measured by intensity of light reflected from a sample illuminated with white light, i.e. the ability of the polypeptide to remove or reduce stains on, e.g., fabrics. The performance may then be quantified by an "Improvement Factor", which is well-known within the knowledge of the skilled person.

In one embodiment, the improved performance is determined according to an AMSA as described in the method section.

Thus, in one embodiment, the improved performance is determined by a method comprising the steps of;
a) washing a fabric stained with starch with an alpha-amylase variant and a parent alpha-amylase sample added, respectively, to a model detergent composition, such as Model A, Model J, Model T, or Model X;
b) measuring the intensity of light reflected from the sample when illuminated with white light; and
c) optionally, calculating the improvement factor (IF) as the ration of delta intensity of the alpha-amylase sample over the delta intensity of the parent alpha-amylase sample.

In one embodiment, the improved performance is determined by a method comprising the steps of;
a) washing a fabric stained with starch with an alpha-amylase variant and a parent alpha-amylase sample added, respectively, to a model detergent composition, such as Model A, Model J, Model T, or Model X, for 20 minutes at 15° C. and 30° C.;
b) measuring the intensity of light reflected from the sample when illuminated with white light; and
c) optionally, calculating the improvement factor (IF) as the ration of delta intensity of the alpha-amylase sample over the delta intensity of the parent alpha-amylase sample.

In a particular embodiment, the variant of the invention has both an improved stability and improved performance in detergent compositions relative to the parent alpha-amylase of SEQ ID NOs: 3 or 13.

Parent Alpha-amylases

The parent alpha-amylase may be (a) a polypeptide having at least 67% sequence identity to the mature polypeptide of SEQ ID NO: 2, or the polypeptide of SEQ ID NOs: 3 or 13; (b) a polypeptide encoded by a polynucleotide that hybridizes under low stringency conditions with (i) the mature polynucleotide coding sequence of SEQ ID NO: 1, or (ii) the full-length complement of (i); or (c) a polynucleotide encoded by a polynucleotide having at least 67% sequence identity to the mature polypeptide coding sequence of SEQ ID NO: 1.

In one embodiment, the parent alpha-amylase has a sequence identity to the mature polypeptide of SEQ ID NO: 2 of at least 67%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one embodiment, the amino acid sequence of the parent differs by up to 10 amino acids, e.g., 1, 2, 3, 4, 5, 6, 7, 8, 9, or 10, from the polypeptide of SEQ ID NOs: 3 or 13.

In another embodiment, the parent alpha-amylase comprises or consists of the amino acid sequence of SEQ ID NO: 2. In another embodiment, the parent comprises or consists of the mature polypeptide of SEQ ID NO: 2. In another embodiment, the parent alpha-amylase comprises or consists of the polypeptide of SEQ ID NO:3. In another embodiment, the parent alpha-amylase comprises or consists of the polypeptide of SEQ ID NO: 13.

In another embodiment, the parent alpha-amylase is a polypeptide which in at least the amino acid positions 51, 109, 193, 201, 269, 294, 297, 298, and 314 when referring to SEQ ID NO: 3 has the amino acids Q, M, N, G, T, M, Q, A, and N, respectively. Accordingly, the amino acid positions of a parent polypeptide as used in relation to the present invention at least have the following amino acids; Q51, M109, N193, G201, T269, M294, Q297, A298, and N314. In a further embodiment, the parent polypeptide has at least 67%, such as at least 70%, at least 75%, at least 80%, at least 85%, at least 90%, at least 95%, at least 96%, at least 97%, at least 98%, at least 99% or 100% sequence identity to the polypeptide of SEQ ID NOs: 3 or 13 but wherein the amino acids in positions 51, 109, 193, 201, 269, 294, 297, 298, and 314 when referring to SEQ ID NO: 3 are the amino acids Q, M, N, G, T, M, Q, A, and N, respectively.

In another embodiment, the parent is a fragment of the polypeptide of SEQ ID NOs: 3 or 13 containing at least 430 amino acid residues, e.g., at least 440, at least 450, at least 460, at least 470, at least 480 amino acid residues.

In another embodiment, the parent is an allelic variant of the polypeptide of SEQ ID NOs: 3 or 13.

In another embodiment, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NOs: 3 or 13, or a fragment thereof may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the full-length complement thereof; or (iii) a subsequence thereof; under very low to very high stringency conditions. Molecules to which the nucleic acid probe hybridizes under these conditions can be detected using, for example, X-ray film or any other detection means known in the art.

In one embodiment, the nucleic acid probe is the mature polypeptide coding sequence of SEQ ID NO: 1. In another embodiment, the nucleic acid probe comprises at least 50% of the nucleotides of SEQ ID NO: 1. In another embodiment, the nucleic acid probe is a polynucleotide that encodes the polypeptide of SEQ ID NO: 2; the mature polypeptide thereof; or a fragment thereof.

In another embodiment, the parent alpha-amylase is encoded by a polynucleotide having a sequence identity to the mature polynucleotide coding sequence of SEQ ID NO: 1 of at least 60%, e.g., at least 67%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The parent may be a fusion polypeptide or cleavable fusion polypeptide in which another polypeptide is fused at the N-terminus or the C-terminus of the polypeptide of the present invention. Thus, the polypeptide may be a hybrid polypeptide in which a region of one polypeptide is fused at the N-terminus or the C-terminus of a region of another polypeptide.

A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly. The parent polypeptide of the present invention has been obtained from an *Alicyclobacillus* species found in humus from a Danish spruce and beech forest.

The parent may be a bacterial alpha-amylase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* alpha-amylase, or a Gram-negative bacterial polypeptide such as a *Campylobacter, E. coli, Flavobacterium, Fusobacterium, Helicobacter, Ilyobacter, Neisseria, Pseudomonas, Salmonella, cytophaga,* or *Ureaplasma* alpha-amylase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis,*

*Bacillus megaterium, Bacillus pumilus, Bacillus stearothermophilus, Bacillus subtilis*, or *Bacillus thuringiensis* alpha-amylase.

In another aspect, the parent is a *Streptococcus equisimilis, Streptococcus pyogenes, Streptococcus uberis*, or *Streptococcus equi* subsp. *Zooepidemicus* alpha-amylase.

In another aspect, the parent is a *Streptomyces achromogenes, Streptomyces avermitilis, Streptomyces coelicolor, Streptomyces griseus*, or *Streptomyces lividans* alpha-amylase.

The parent may be a fungal alpha-amylase. For example, the parent may be a yeast alpha-amylase such as a *Candida, Kluyveromyces, Pichia, Saccharomyces, Schizosaccharomyces*, or *Yarrowia* alpha-amylase; or a filamentous fungal alpha-amylase such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* alpha-amylase.

In another aspect, the parent is a *Saccharomyces carlsbergensis, Saccharomyces cerevisiae, Saccharomyces diastaticus, Saccharomyces douglasfi, Saccharomyces kluyveri, Saccharomyces norbensis*, or *Saccharomyces oviformis* alpha-amylase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonaturn, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* alpha-amylase.

In another aspect, the parent is an *Alicyclobacillus* alpha-amylase, e.g., the alpha-amylase of SEQ ID NO: 2 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent alpha-amylase may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample.

Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to a method of producing an alpha-amylase of the invention, comprising (a) cultivating a host cell under conditions suitable for expression of the variant of the invention, and (b) recovering the variant.

The present invention also relates to methods for obtaining an alpha-amylase variant, comprising introducing into a parent alpha-amylase having at least 67% sequence identity to the polypeptide of SEQ ID NOs: 3 or 13 a substitution at one or more positions said substitutions corresponding to positions 51, 109, 193, 201, 269, 294, 297, 298 and 314 of SEQ ID NO: 3, wherein the variant has alpha-amylase activity; and recovering said variant.

In a particular embodiment, the present invention relates to methods for obtaining a variant having alpha-amylase activity, comprising: (a) introducing into a parent alpha-amylase having at least 67% sequence identity to the polypeptide of SEQ ID NOs: 3 or 13 a substitution at one or more positions said substitutions corresponding to positions 109, 51, 201, 269, 294, 297, 298, 193, and 314 of SEQ ID NO:3, wherein the variant has at least 67%, such as at least 70%, such as at least 75%, such as at least 80%, such as at least 85%, such as at least 90%, such as at least 95%, such as at least 96%, such as at least 97%, such as at least 99%, but less than 100% sequence identity with the amino acid sequence of SEQ ID NOs: 3 or 13, wherein the variant has alpha-amylase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

The present invention furthermore relates to methods of producing an alpha-amylase variant, comprising: (a) cultivating a host cell of the present invention under conditions suitable for expression of the alpha-amylase variant; and (b) recovering the alpha-amylase variant.

Thus, in one aspect, the present invention relates to a method of producing an alpha-amylase variant, comprising a) cultivating a host cell as described herein under conditions suitable for expression of the variant, and b) recovering the variant. In a particular embodiment, the method of producing an alpha-amylase variant comprises the steps of a) cultivating a host cell comprising a polynucleotide, a nucleic acid construct or an expression vector as described herein; b) recovering the variant. In one embodiment, the method of producing an alpha-amylase variant comprises the steps of a) cultivating a host cell comprises a polynucleotide encoding an alpha-amylase variant comprising a substitution in one or more positions corresponding to positions 51, 109, 193, 201, 269, 294, 297, 298, and 314 of SEQ ID NO:3, a nucleic acid construct encoding an alpha-amylase variant comprising a substitution in one or more positions corresponding to positions 51, 109, 193, 201, 269, 294, 297, 298, and 314 of SEQ ID NO:3, or an expression vector encoding an alpha-amylase variant comprising a substitution in one or more positions corresponding to positions 51, 109, 193, 201, 269, 294, 297, 298, and 314 of SEQ ID NO:3; and b) recovering the variant. The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants having alpha-amylase activity. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

In one aspect, the present invention relates to a method of improving the stability, in particular the detergent stability, preferably liquid detergent stability, of a parent alpha-amylase having the amino acid sequence of SEQ ID NO:3, or having at least 67% sequence identity thereto, wherein the method comprises the steps of:
  a) a substitution at one or more positions said substitutions corresponding to positions 51, 109, 193, 201, 269, 294, 297, 298, and 314 of SEQ ID NO:3 when using the mature polypeptide of SEQ ID NO:3 for numbering, wherein the resulting variant has at least 67%, such as at least 70%, such as at least 75%, such as at least 80%, such as at least 85%, such as at least 90%, such as at least 95%, such as at least 96%, such as at least 97%, such as at least 99%, but less than 100% sequence identity with the amino acid sequence of SEQ ID NOs: 3 or 13, where the variant has alpha-amylase activity; and b) introducing into the parent alpha-amylase one or more of the following substitutions; 105L,I,F+206Y; 105L, I+206Y+217I; 105F+206Y+208Y+217V+246V; 105L+206F; 105I+206Y+208Y+217I+246V; 195F+ 213S+214T; 195F+206Y+208Y+213T+214T+217M, V; 195F+206Y+208F,L+213T+214T+217V; 195F+ 206Y+213S+214T; 195F+206Y+208Y+213S+214T+ 217M; 195F+206Y+208F+213T+214T+217M; 195F+ 206Y+208Y+213T+214T+217Q; 195F+206Y+213G+ 214T; 195F+206Y+213S; 195F+206Y+208Y+213T+ 214T+217M; 195F+213S; 195F+206Y+208L+213T+ 214T+217M; 195F+213G+214T; 206Y,F+208Y+ 217Q; 206Y+208Y+217I; 206F+208Y+217M; 206Y+ 208Y; 206Y+217M; 206Y+208Y+213A+217M; 206Y+208Y+217V+246V; 206Y+213G; 206Y+208F+ 217V; 206N+208Y+217M; 206F+208Y+217V; 206Y+ 246V; 206Y+217I,V; 206F+208F+217I; 206Y+208L+ 213S; 206F+217I; 206Y+217I+246I; 206L+217V; 206Y+208F+217H; 206L+208F+217I; 206L+217V+ 246L; 206F+246V; 208Y+213S+217M; 208Y+213A+ 217Q; 63I+206Y; 63I+206Y+241V; 63V+206Y; 63V+ 105L+206Y; 63V+206Y+217I; 63V+105F+206Y+ 208F+217I; 63V+206Y+246V; 63V+206F; 63V+ 206L+217V; 63V+105F+206Y; 63V+206Y+241V+ 246L; 195F+206Y+208Y+214T+217V; 186E+195F+ 206Y; 195F+206Y+208Y+213T+217V; 186E+195F+ 202T+206Y+209S; 63I+195F+206Y+210S; 195F+ 206Y+213P+214T; 195F+206Y+208Y+213T+214T+ 217I; 186E+195F+206Y+210S; 195F+213P; 186E+ 195F+202T+206Y+210S; 195F+206H; 195F+208Y+ 213T+214T+217V; 206Y+208Y+213T+214T+217V; 195F+206Y+217V; 195F+206Y+208Y+213S+214T; 195F+206Y+208Y; 195F+213I+214P; 195F+206Y+ 208Y+213T+214T; 195F+206Y; 206Y+213S; 182P+ 186E; 182S+186E; 182V+186K; 179L+186H+190P; 179L+186K,R,S+190P; 179L+190P; 179L+182C+ 186K+190P; 179L+182P+186S,V+190P; 179L+182S+ 186Q+190P; 173F+174Q; 173Y+174S; 172K+173Y+ 174E; 193A,D,N,S+195F; 213A+214Q; 213P+214L; 213S+214R; 48V+60V; 213G+214T; 213I+214P; 213N+214I; 213N+214Q, and 213P,S+214T, wherein numbering is according to SEQ ID NO:11, and wherein the resulting variant has at least 67%, such as at least 70%, at least 75%, at least 80%, at least 85%, at least 90%, at least 95%, at least 97%, at least 98%, at least 99%, but less than 100% sequence identity with the polypeptide of SEQ ID NOs: 3 or 13, and wherein the variant has alpha-amylase activity and improved detergent stability and/or improved performance compared to the parent alpha-amylase.

In a further embodiment, the variant has at least 50%, such as at least 60%, or at least 70%, or at least 80%, or at least 90%, or at least 100% of the activity of the parent alpha-amylase having the amino acid sequence of SEQ ID NOs: 3 or 13.

In a further embodiment, the activity is determined according to the Phadebas assay as described herein. Thus, in one embodiment, the activity is determined by a method comprising the steps of;

a) incubating an alpha-amylase variant according to the invention with a dyed amylose substrate for 15 minute at 37° C.; and b) measuring the absorption at OD 620 nm.

In a further embodiment, the activity is determined by a method comprising the steps of;

a) incubating an alpha-amylase variant according to the invention with a dyed amylose substrate for 15 minute at 37° C.; and b) centrifuging the sample;

c) transferring the supernatant to reader plate, and d) measuring the absorption at OD 620 nm.

Polynucleotides

The present invention also relates to polynucleotides encoding a variant of the present invention. Thus, in one aspect, the present invention relates to a polynucleotide encoding a variant as described herein. In one embodiment, the polynucleotide is an isolated polynucleotide.

In a particular embodiment, the polynucleotide encodes an alpha-amylase variant comprising a substitution at one or more positions corresponding to positions 51, 109, 193, 201, 269, 294, 297, 298, and 314 of SEQ ID NO:3.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Thus, in one embodiment, the invention relates to a nucleic acid construct comprising a polynucleotide as described herein. In a particular embodiment, the nucleic acid construct comprises a polynucleotide encoding an alpha-amylase variant as described herein. Thus, the nucleic acid construct comprises a polynucleotide encoding a variant comprising a substitution at one or more positions corresponding to positions 51, 109, 193, 201, 269, 294, 297, 298, and 314 of SEQ ID NO:3.

The term "nucleic acid construct" as used herein, refers to a DNA construct which is an artificially constructed segment of nucleic acids to be transplanted into target tissue or cell, such as a host cell. A nucleic acid construct comprises at least a gene sequence encoding the polypeptide. It is within the skills of the skilled person to understand the meaning and purpose of a nucleic acid construct.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylllA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (g!aA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an Aspergillus neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausfi* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The term "expression vector" as used herein, refers to any vector which may comprise an origin of replication, a selectable marker, and a suitable site for the insertion of a gene such as the multiple cloning site. The cloned gene may be transferred from a specialized cloning vector to an expression vector, although it is possible to clone directly into an expression vector. It is within the skills of the skilled person to determine the meaning and purpose of an expression vector.

Accordingly, in one aspect, the present invention relates to an expression vector comprising a polynucleotide as described herein. Thus, in a particular embodiment, the expression vector comprises a polynucleotide encoding an alpha-amylase variant comprising a substitution at one or more positions corresponding to positions 51, 109, 193, 201, 269, 294, 297, 298, and 314 of SEQ ID NO:3.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

Accordingly, in one aspect the present invention relates to a host cell comprising a polynucleotide, a nucleic acid construct or an expression vector as described herein. Thus, in one embodiment, the host cell comprises a polynucleotide encoding an alpha-amylase variant comprising a substitution in one or more positions corresponding to positions 51, 109, 193, 201, 269, 294, 297, 298, and 314 of SEQ ID NO:3, a nucleic acid construct encoding an alpha-amylase variant comprising a substitution in one or more positions corresponding to positions 51, 109, 201, 269, 294, 297, 298, and 314 of SEQ ID NO:3, or an expression vector encoding an alpha-amylase variant comprising a substitution in one or more positions corresponding to positions 51, 109, 201, 269, 294, 297, 298, and 314 of SEQ ID NO:3.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any Streptococcus cell including, but not limited to, *Streptococcus equisimilis, Streptococcus pyogenes, Streptococcus uberis*, and *Streptococcus equi* subsp. *Zooepidemicus* cells.

The bacterial host cell may also be any Streptomyces cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a Streptomyces cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chtysosporium queenslandicum, Chtysosporium tropicum, Chtysosporium zonaturn, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Fermentation Broth Formulations or Cell Compositions

The present invention also relates to a fermentation broth formulation or a cell composition comprising a polypeptide of the present invention. Thus, in one embodiment, the fermentation broth formulation or the cell composition comprises a polynucleotide encoding an alpha-amylase variant comprising a substitution in one or more positions corresponding to positions 51, 109, 193, 201, 269, 294, 297, 298, and 314 of SEQ ID NO:3, a nucleic acid construct encoding an alpha-amylase variant comprising a substitution in one or more positions corresponding to positions 51, 109, 193, 201, 269, 294, 297, 298, and 314 of SEQ ID NO:3, or an expression vector encoding an alpha-amylase variant comprising a substitution in one or more positions corresponding to positions 51, 109, 193, 201, 269, 294, 297, 298, and 314 of SEQ ID NO:3. The fermentation broth product may further comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a particular embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one embodiment, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may comprise the unfractionated contents of the fermentation materials derived at the end of the fermentation. Typically, the cell-killed whole broth or composition comprises the spent culture medium and cell debris present after the microbial cells (e.g., filamentous fungal cells) are grown to saturation, incubated under carbon-limiting conditions to allow protein synthesis. In some embodiments, the cell-killed whole broth or composition comprises the spent cell culture medium, extracellular enzymes, and killed filamentous fungal cells. In some embodiments, the microbial cells present in the cell-killed whole broth or composition may be permeabilized and/or lysed using methods known in the art.

A whole broth or cell composition as described herein is typically a liquid, but may comprise insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising an alpha-amylase variant of the present invention. Thus, in one aspect the present invention relates to a composition comprising an alpha-amylase variant as described herein. In a particular embodiment, the composition comprises a variant which comprises a substitution in one or more positions corresponding to position 51, 109, 193, 201, 269, 294, 297, 298, and 314 of SEQ ID NO:3. Preferably, the compositions are enriched in such a variant. The term "enriched" indicates that the alpha-amylase activity of the composition has been increased, e.g., with an enrichment factor of at least 1.1.

The compositions may comprise a variant of the present invention as the major enzymatic component, e.g., a mono-component composition. In another embodiment, the composition comprises at least one further active component.

The term "active component" as used herein, refers to any biological or non-biological molecule which in itself is active. For example, an active component is an enzyme.

Thus, in one embodiment, the further active component is an enzyme, such as a protease, lipase, cellulose, pectate lyase, and mannanase. Thus, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In a particular embodiment, the further active component is an enzyme, which is selected from the group consisting of;

i. a protease comprising one or more modifications in the following positions: 32, 33, 48-54, 58-62, 94-107, 116, 123-133, 150, 152-156, 158-161, 164, 169, 175-186, 197, 198, 203-216 as compared with the protease in SEQ ID NO:4;

ii. a lipase comprising one or more modifications in the following positions: 1-5, 27, 33, 38, 57, 91, 94, 96, 97, 111, 163, 210, 225, 231, 233, 249, and 254-256 as compared with the lipase in SEQ ID NO:5;

iii. an alpha-amylase comprising one or more modifications in the following positions: 9, 118, 149, 182, 186, 195, 202, 257, 295, 299, 320, 323, 339, 345, and 458 as compared with the alpha-amylase in SEQ ID NO:6;

iv. an alpha-amylase comprising one or more modifications in the following positions: 140, 195, and 206, 243, 260, and 476 as compared with the alpha-amylase in SEQ ID NO:7;

v. an alpha-amylase comprising one or more modifications in the following positions: 180, 181, 243, and 475 as compared with the alpha-amylase in SEQ ID NO:8;

vi. an alpha-amylase comprising one or more modifications in the following positions: 178, 179, 187, 203, 458, 459, 460, and 476 as compared with the alpha-amylase in SEQ ID NO:9;

vii. an alpha-amylase comprising a modifications in the following position: 202 as compared with the alpha-amylase in SEQ ID NO:10;

viii. an alpha-amylase comprising one or more modifications in the following positions: 405, 421, 422, and 428 as compared with the alpha-amylase in SEQ ID NO:11; and/or ix. an alpha-amylase according to SEQ ID NO:12.

The detergent composition may comprise one or more additional enzymes, herein also termed "further active components", such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Example of cellulases exhibiting endo-beta-1,4-glucanase activity (EC 3.2.1.4) are those having described in WO02/099091.

Other examples of cellulases include the family 45 cellulases described in WO96/29397, and especially variants thereof having substitution, insertion and/or deletion at one or more of the positions corresponding to the following positions in SEQ ID NO: 8 of WO 02/099091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146 R.

Commercially available cellulases include Celluzyme, and Carezyme (Novozymes A/S), Clazinase, and Puradax HA (Genencor International Inc.), and KAC-500(B) (Kao Corporation).

The additional enzyme (or further active component) may be a protease or protease variant. The protease may be of animal, vegetable or microbial origin, including chemically or genetically modified mutants. Microbial origin is preferred. It may be an alkaline protease, such as a serine protease or a metalloprotease. A serine protease may for example be of the S1family, such as trypsin, or the S8 family such as subtilisin. A metalloproteases protease may for example be a thermolysin from e.g. family M4, M5, M7 or M8.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. In one aspect of the invention the protease may be a subtilase, such as a subtilisin or a variant hereof. Further the subtilases (and the serine proteases) are characterised by having two active site amino acid residues apart from the serine, namely a histidine and an aspartic acid residue.

Examples of subtilisins are those derived from Bacillus such as subtilisin lentus, Bacillus lentus, subtilisin Novo, subtilisin Carlsberg, Bacillus licheniformis, subtilisin BPN', subtilisin 309, subtilisin 147 and subtilisin 168 described in WO 89/06279 and protease PD138 (WO 93/18140). Additional serine protease examples are described in WO 98/020115, WO 01/44452, WO 01/58275, WO 01/58276, WO 03/006602 and WO 04/099401. An example of a subtilase variants may be those having mutations in any of the positions: 3, 4, 9, 15, 27, 36, 68, 76, 87, 95, 96, 97, 98, 99, 100, 101, 102, 103, 104, 106, 118, 120, 123, 128, 129, 130, 160, 167, 170, 194, 195, 199, 205, 217, 218, 222, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G, M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering). A further preferred protease is the alkaline protease from Bacillus lentus DSM 5483, as described for example in WO 95/23221, and variants thereof which are described in WO 92/21760, WO 95/23221, EP 1921147 and EP 1921148.

Examples of trypsin-like proteases are trypsin (e.g. of porcine or bovine origin) and the Fusarium protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Examples of metalloproteases are the neutral metalloprotease as described in WO 07/044993.

Preferred commercially available protease enzymes include Alcalase™, Coronase™, Duralase™, Durazym™, Esperase™, Everlase™, Kannase™, Liquanase™, Liquanase Ultra™, Ovozyme™, Polarzyme™, Primase™, Relase™, Savinase™ and Savinase Ultra™, (Novozymes A/S), Axapem™ (Gist-Brocases N.V.), BLAP and BLAP X (Henkel AG & Co. KGaA), Excellase™, FN2™, FN3™, FN4™, Maxaca™, Maxapem™, Maxatase™, Properase™, Purafast™, Purafect™, Purafect OxP™, Purafect Prime™ and Puramax™ (Genencor int.).

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP258068 and EP305216, cutinase from Humicola, e.g. H. insolens (WO96/13580), lipase from strains of Pseudomonas (some of these now renamed to Burkholderia), e.g. P. alcaligenes or P. pseudoalcaligenes (EP218272), P. cepacia (EP331376), P. sp. strain SD705 (WO95/06720 & WO96/27002), P. wisconsinensis (WO96/12012), GDSL-type Streptomyces lipases (WO10/065455), cutinase from Magnaporthe grisea (WO10/107560), cutinase from Pseudomonas mendocina (U.S. Pat. No. 5,389,536), lipase from Thermobifida fusca (WO11/084412), Geobacillus stearothermophilus lipase (WO11/084417), lipase from Bacillus subtilis (WO11/084599), and lipase from Streptomyces griseus (WO11/150157) and S. pristinaespiralis (WO12/137147).

Further examples are lipases sometimes referred to as acyltransferases or perhydrolases, e.g. acyltransferases with homology to Candida antarctica lipase A (WO10/111143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100028).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

The further active component is not limited to other categories of enzymes. Thus, the further active component may be an additional amylase such as an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Examples of amylases are those described in WO 95/10603 or variants thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 of SEQ ID NO: 3 in WO 95/10603. Other amylases which can be used are amylases having SEQ ID NO: 6 in WO 02/010355 or variants thereof as well as hybrid alpha-amylase comprising residues 1-33 of the alpha-amylase derived from *Bacillus amyloliquefaciens* shown in SEQ ID NO: 6 of WO 2006/066594 and residues 36-483 of the *Bacillus licheniformis* alpha-amylase shown in SEQ ID WO: 4 of WO 2006/066594.

Further amylase examples are amylases having SEQ ID NO: 6 in WO 99/019467 or variants thereof and amylases having SEQ ID NO: 1, SEQ ID NO: 2 or SEQ ID NO: 7 of WO 96/023873 or variants thereof. Other amylases which can be used are amylases having SEQ ID NO: 2 of WO 08/153815, SEQ ID NO: 10 in WO 01/66712 or variants thereof.

Additional amylases which can be used are amylases having SEQ ID NO: 2 of WO 09/061380 or variants thereof and alpha-amylases having SEQ ID NO: 12 in WO01/66712 or a variant thereof.

Commercially available amylases are Duramyl, Termamyl, Fungamyl, Stainzyme, Stainzyme Plus, Natalase, BAN, Everest and Amplify (Novozymes A/S), Powerase, Preferenz S100, Preferenz S110, Preferenz S1000, Preferenz S2000, Excellenz S1000 (from Genencor International Inc.).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The compositions may be prepared in accordance with methods known in the art and may be in the form of a liquid or a dry composition. The compositions may be stabilized in accordance with methods known in the art.

Detergent Compositions

In one aspect, the invention relates to detergent compositions comprising an alpha-amylase variant as described herein. Thus, in one aspect the invention relates to a composition which is a detergent composition. In a particular embodiment, the detergent composition is a liquid or powder composition. In one embodiment, the composition comprises an alpha-amylase variant which comprises a substitution in one or more positions corresponding to positions 51, 109, 193, 201, 269, 294, 297, 298, and 314 of SEQ ID NO: 3. In a further embodiment, the composition comprises a detergent composition of the present invention in combination with one or more additional cleaning composition components. In an embodiment, the detergent is a liquid detergent composition. In another embodiment the detergent composition is a powder detergent composition.

The detergent composition may be a laundry detergent composition or a dish wash detergent composition. A dish wash detergent composition may be both for use in manual dish wash as well as for use in automated dish wash.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment of the present invention, the a polypeptide of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor. The term "protein" in this context is contemplated to be understood to include an alpha-amylase variant according to the present invention.

A composition for use in automatic dish wash (ADW), for example, may include 0.0001%-50%, such as 0.001%-20%, such as 0.01%-10%, such as 0.05-5% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The alpha-amylase variants of the invention as well as the further active components, such as additional enzymes, may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. Such detergent compositions are all embodiments of the invention.

An alpha-amylase variant of the present invention may also be incorporated in the detergent formulations disclosed in WO97/07202, which is hereby incorporated by reference.

Examples are given herein of preferred uses of the compositions of the present invention. The dosage of the composition and other conditions under which the composition is used may be determined on the basis of methods known in the art.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 40% by weight of a cationic surfactant. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0% to about 40% by weight of a zwitterionic surfactant. Non-limiting examples of zwitterionic surfactants include betaine, alkyldimethylbetaine, sulfobetaine, and combinations thereof.

The detergent composition may also comprise one or more isoprenoid surfactants as disclosed in US 20130072416 or US 20130072415.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 10% to about 40% of a detergent builder or co-builder, or a mixture thereof. In a dish wash detergent, the level of builder is typically 40-65%, particularly 50-65%. The builder and/or co-builder may particularly be a chelating agent (ie. a chelator) that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2', 2"-nitrilotriethanol), and carboxymethyl inulin (CMI), and combinations thereof.

The detergent composition may also contain 0-50% by weight, such as about 10% to about 40%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2', 2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (a-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)-ethylidenediamine-N, N', N'-triacetate (HEDTA), diethanolglycine (DEG), diethylenetriamine penta (methylenephosphonic acid) (DTPMP), aminotris (methylenephosphonic acid) (ATMP), and combinations and salts thereof. Further exemplary builders and/or co-builders are described in, e.g., WO 09/102854, U.S. Pat. No. 5,977,053.

Chelating agents or chelators are chemicals which form molecules with certain metal ions, inactivating the ions so that they cannot react with other elements thus a binding agent that suppresses chemical activity by forming chelates. Chelation is the formation or presence of two or more separate bindings between a ligand and a single central atom. The ligand may be any organic compound, a silicate or a phosphate. In the present context the term "chelating agents" comprises chelants, chelating agent, chelating agents, complexing agents, or sequestering agents that forms water-soluble complexes with metal ions such as calcium and magnesium.

The chelate effect describes the enhanced affinity of chelating ligands for a metal ion compared to the affinity of a collection of similar nonchelating ligands for the same metal. Chelating agents having binding capacity with metal ions, in particular calcium (Ca2+) ions, and has been used widely in detergents and compositions in general for wash, such as laundry or dish wash. Chelating agents have however shown themselves to inhibit enzymatic activity. The term chelating agent is used in the present application interchangeably with "complexing agent" or "chelating agent" or "chelant".

Since most alpha-amylases are calcium sensitive the presence of chelating agents these may impair the enzyme activity. The calcium sensitivity of alpha-amylases can be determined by incubating a given alpha-amylase in the presence of a strong chelating agent and analyze the impact of this incubation on the activity of the alpha-amylase in question. A calcium sensitive alpha-amylase will lose a major part or all of its activity during the incubation. Chelating agent may be present in the composition in an amount from 0.0001 wt % to 20wt %, preferably from 0.01 to 10 wt %, more preferably from 0.1 to 5wt %.

Strong chelating agents may be but are not limited to the following: ethylene-diamine-tetra-acetic acid (EDTA), diethylene triamine penta methylene phosphonic acid (DTMPA, DTPMP), hydroxy-ethane diphosphonic acid (HEDP), ethylenediamine N,N'-disuccinic acid (EDDS), methyl glycine di-acetic acid (MGDA), diethylene triamine penta acetic acid (DTPA), propylene diamine tetraacetic acid (PDTA), 2-hydroxypyridine-N-oxide (HPNO), methyl glycine diacetic acid (MGDA), glutamic acid N,N-diacetic acid (N,N-dicarboxymethyl glutamic acid tetrasodium salt (GLDA) and nitrilotriacetic acid (NTA) or mixtures thereof. The chelating agents may be present in their acid form or a salt, preferably the chelating agents may be present as a sodium, ammonium or potassium salt.

Characterizing chelating agents: As mentioned the chelate effect or the chelating effect describes the enhanced affinity of chelating ligands for a metal ion compared to the affinity of a collection of similar nonchelating ligands for the same metal. However, the strength of this chelate effect can be determined by various types of assays or measure methods thereby differentiating or ranking the chelating agents according to their chelating effect (or strength).

In an assay the chelating agents may be characterized by their ability to reduce the concentration of free calcium ions (Ca2+) from 2.0 mM to 0.10 mM or less at pH 8.0, e.g. by using a test based on the method described by M. K. Nagarajan et al., JAOCS, Vol. 61, no. 9 (September 1984), pp. 1475-1478.

For reference, a chelator having the same ability to reduce the concentration of free calcium ions (Ca2+) from 2.0 mM to 0.10 mM at pH as EDTA at equal concentrations of the chelator are said to be strong chelators.

Bleaching Systems

The detergent may contain 0-20% by weight, such as about 0% to about 10%, of a bleaching system. Any bleaching system known in the art for use in laundry+dish wash+ l&I detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO098/17767. A particular family of bleach activators of interest was disclosed in EP624154 and particulary preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

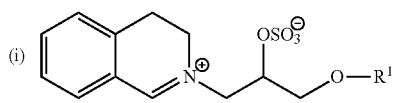

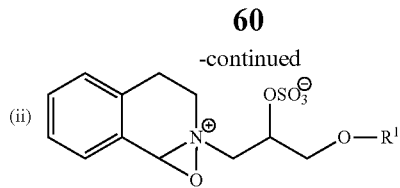

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g. in WO2007/087258, WO2007/087244, WO2007/087259 and WO2007/087242. Suitable photobleaches may for example be sulfonated zinc phthalocyanine.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers , hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

The detergent compositions of the present invention may also comprise dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The detergent compositions of the present invention may preferably also comprise additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4''-naptho-1.,2':4,5)-1,2,3-trizole-2''-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

The detergent compositions of the present invention may also comprise one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

The detergent compositions of the present invention may also comprise one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivatives thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients may be separated physically from each other by compartments in water dissolvable pouches or in different layers of tablets. Thereby negative storage interaction between components may be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may comprise one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be e.g. $Na^+$, $K^+$ or $NH_4^+$ and the organic anion may be for example formate, acetate, citrate or lactate such that the salt of a monovalent cation and an organic anion may be, for example, sodium formate.

The laundry soap bar may also comprise complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix comprising a soap, an enzyme, optionally one or more additional enzymes, a protease inhibitor, and a salt of a monovalent cation and an organic anion may be prepared and the mixture may then plodded. The enzyme and optional additional enzymes may be added at the same time as an enzyme inhibitor, e.g. a protease inhibitor, for example in liquid form. Besides the mixing step and the plodding step, the process may further comprise the steps of milling, extruding, cutting, stamping, cooling and/or wrapping.

Granular Detergent Formulations

A granular detergent may be formulated as described in WO09/092699, EP1705241, EP1382668, WO07/001262, U.S. Pat. No, 6472364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, WO09/015951, WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905, WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792, WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, and WO2010000636.

Method of Producing the Composition

The present invention also relates to methods of producing the composition. The method may be relevant for the (storage) stability of the detergent composition: e.g. soap bar premix method WO2009155557.

Uses

The present invention is directed to methods for using the alpha-amylase variants, or compositions thereof, in a cleaning process such as laundry or hard surface cleaning including automated dish wash. The soils and stains that are important for cleaning are composed of many different substances, and a range of different enzymes, all with different substrate specificities, have been developed for use in detergents both in relation to laundry and hard surface cleaning, such as dishwashing. These enzymes are considered to provide an enzyme detergency benefit, since they specifically improve stain removal in the cleaning process that they are used in, compared to the same process without enzymes. Stain removing enzymes that are known in the art include enzymes such as proteases, amylases, lipases, cutinases, cellulases, endoglucanases, xyloglucanases, pectinases, pectin lyases, xanthanases, peroxidaes, haloperoxygenases, catalases and mannanases.

In one aspect, the invention relates the use of alpha-amylases variants of the present invention in detergent compositions, for use in cleaning hard-surfaces, such as dish wash, or in laundering or for stain removal. In another aspect, the invention relates to the use of an alpha-amylase variant according to the invention in a cleaning process such as laundry or hard surface cleaning including, but not limited to, dish wash and industrial cleaning. Thus, in one embodiment, the invention relates to the use of an alpha-amylase variant comprising a substitution in one or more positions corresponding to positions 51, 109, 193, 201, 269, 294, 297, 298, and 314 of SEQ ID NO:3 in a cleaning process such as laundry or hard surface cleaning including dish wash and industrial cleaning.

In one embodiment of the invention relates the use of the detergent composition comprising an alpha-amylase variant of the present invention together with one or more surfactants and optionally one or more detergent components, selected from the list comprising of hydrotropes, builders and co-builders, bleaching systems, polymers, fabric hueing agents and adjunct materials, or any mixture thereof in detergent compositions and in detergent applications.

A further embodiment is the use of the detergent composition comprising an alpha-amylase of the present invention together with one or more surfactants, and one or more additional enzymes selected from the group comprising of proteases, lipases, cutinases, cellulases, endoglucanases, xyloglucanases, pectinases, pectin lyases, xanthanases, peroxidaes, haloperoxygenases, catalases and mannanases, or any mixture thereof in detergent compositions and in detergent applications.

In another aspect, the invention relates to a laundering process which may be for household laundering as well as industrial laundering. Furthermore, the invention relates to a process for the laundering of textiles (e.g. fabrics, garments, cloths etc.) where the process comprises treating the textile with a washing solution containing a detergent composition and an alpha-amylase of the present invention. The laundering can for example be carried out using a household or an industrial washing machine or be carried out by hand using a detergent composition containing a glucoamylase of the invention.

In another aspect, the invention relates to a dish wash process which may be for household dish wash as well as industrial dish wash. The term "dish wash" as used herein, refers to both manual dish wash and automated dish wash. Furthermore, the invention relates to a process for the washing of hard surfaces (e.g. cutlery such as knives, forks, spoons; crockery such as plates, glasses, bowls; and pans) where the process comprises treating the hard surface with a washing solution containing a detergent composition and an alpha-amylase variant of the present invention. The hard surface washing can for example be carried out using a household or an industrial dishwasher or be carried out by hand using a detergent composition containing an alpha-amylase of the invention, optionally together with one or more further enzymes selected from the group comprising of proteases, amylases, lipases, cutinases, cellulases, endoglucanases, xyloglucanases, pectinases, pectin lyases, xanthanases, peroxidaes, haloperoxygenases, catalases, mannanases, or any mixture thereof.

In a further aspect, the invention relates to a method for removing a stain from a surface comprising contacting the surface with a composition comprising an alpha-amylase of the present invention together with one or more surfactants and optionally one or more detergent components selected from the list comprising of hydrotropes, builders and co-builders, bleaching systems, polymers, fabric hueing agents and adjunct materials, or any mixture thereof in detergent compositions and in detergent applications. A further aspect is a method for removing a stain from a surface comprising contacting the surface with a composition comprising an alpha-amylase variant of the present invention together with one or more surfactants, one or more additional enzymes selected from the group comprising of proteases, lipases, cutinases, cellulases, endoglucanases, xyloglucanases, pectinases, pectin lyases, xanthanases, peroxidaes, haloperoxygenases, catalases and mannanases, or any mixture thereof in detergent compositions and in detergent applications.

pNP-G7 Assay—Alpha-amylase Activity

The alpha-amylase activity may be determined by a method employing the G7-pNP substrate. G7-pNP which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473).

Reagents:

The G7-pNP substrate from this kit contains 22 mM 4,6-ethylidene- G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, >4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)_n$ (n=9-10))), 1 mM CaCl2, pH8.0.

Procedure:

The amylase sample to be analyzed is diluted in dilution buffer to ensure the pH in the diluted sample is 7. The assay is performed by transferring 20 μl diluted enzyme samples to 96 well microtiter plate and adding 80 μl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Phadebas Activity Assay

The alpha-amylase activity can also be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample.

The alpha-amylase sample to be analyzed is diluted in activity buffer with the desired pH. Two substrate tablets are suspended in 5 mL activity buffer and mixed on magnetic stirrer. During mixing of substrate transfer 150 μl to microtiter plate (MTP) or PCR-MTP. Add 30 μl diluted amylase sample to 150 μl substrate and mix. Incubate for 15 minutes at 37° C. The reaction is stopped by adding 30 μl M NaOH and mix. Centrifuge MTP for 5 minutes at 4000×g. Transfer 100 μl to new MTP and measure absorbance at 620 nm.

The alpha-amylase sample should be diluted so that the absorbance at 620 nm is between 0 and 2.2, and is within the linear range of the activity assay.

Amylazyme Activity Assay

The alpha-amylase activity may also be determined by a method using the Amylazyme substrate (Megazyme® Amylazyme Test, supplied by Megazyme for the assay of cereal and bacterial amylases) comprising AZCL-amylose, which has been mixed with lactose and magnesium stearate and tabletted. A blue dye is covalently bound to these microspheres. The interlinked amylose polymers in the microsphere are degraded at a speed that is proportional to the alpha-amylase activity. When the alpha-amylase degrades the starch polymers, the released blue dye is water soluble and concentration of dye may be determined by measuring absorbance at 590 nm. The concentration of blue is proportional to the alpha-amylase activity in the sample.

The alpha-amylase sample to be analyzed is diluted in activity buffer with the desired pH. Two substrate tablets are suspended in 5 mL activity buffer and mixed on magnetic stirrer. During mixing of substrate 150 μl is transferred to a microtiter plate (MTP) or PCR-MTP. Next, 25 μl diluted amylase sample is added to 150 μl substrate and mixed. The mixture is incubated for 10 minutes at 37° C. The reaction is stopped by adding 25 μl 1M NaOH and mixed. MTP is centrifuged for 5 minutes at 4000×g, followed by transferring 100 μl to a new MTP and absorbance is measured at 590 nm.

The alpha-amylase sample may be diluted so that the absorbance at 590 nm is between 0 and 2.2, and is within the linear range of the activity assay.

Reducing Sugar Activity Assay

The alpha-amylase activity can also be determined by reducing sugar assay with for example corn starch substrate. The number of reducing ends formed by the alpha-amylase hydrolysing the alpha-1,4-glycosidic linkages in starch is determined by reaction with p-Hydroxybenzoic acid hydrazide (PHBAH). After reaction with PHBAH the number of reducing ends can be measured by absorbance at 405 nm and the concentration of reducing ends is proportional to the alpha-amylase activity in the sample.

The corns starch substrate (3 mg/ml) is solubilised by cooking for 5 minutes in milliQ water and cooled down before assay. For the stop solution prepare a Ka-Na-tartrate/NaOH solution (K—Na-tartrate (Merck 8087) 50 g/l, NaOH 20 g/l ) and prepare freshly the stop solution by adding p-Hydroxybenzoic acid hydrazide (PHBAH, Sigma H9882) to Ka-Na-tartrate/NaOH solution to 15 mg/ml.

In PCR-MTP 50 μl activity buffer is mixed with 50 μl substrate. Add 50 μl diluted enzyme and mix. Incubate at the desired temperature in PCR machine for 5 minutes. Reaction is stopped by adding 75 μl stop solution (Ka-Na-tartrate/NaOH/PHBAH). Incubate in PCR machine for 10 minutes at 95° C. Transfer 150 μl to new MTP and measure absorbance at 405 nm. The alpha-amylase sample should be diluted so that the absorbance at 405 nm is between 0 and 2.2, and is within the linear range of the activity assay.

EnzChek® Assay

For the determination of residual amylase activity an EnzChek® Ultra Amylase Assay Kit (E33651, Invitrogen, La Jolla, Calif., USA) may be used.

The substrate is a corn starch derivative, DQ® starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Wash Performance of Alpha-amylases using Automatic Mechanical Stress Assay (AMSA)

In order to assess the wash performance of the polypeptides in a detergent base composition, washing experiments may be performed using Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740, especially the paragraph "Special method embodiments" at page 23-24.

General Laundry Wash Performance Description

A test solution comprising water (6° dH), 0.79 g/L detergent, e.g. model detergent J as described below, and the polypeptide, i.e. enzyme, of the invention at concentration of 0 or 0.6 mg enzyme protein/L, is prepared. Fabrics stained with starch (CS-28 from Center For Test materials BV, P.O. Box 120, 3133 KT, Vlaardingen, The Netherlands) is added and washed for 20 minutes at 15° C. and/or 30° C., or alternatively 20 minutes at 15° C. and/or 40° C. as specified in the examples. After thorough rinse under running tap water and drying in the dark, the light intensity values of the stained fabrics are subsequently measured as a measure for wash performance. The test with 0 mg enzyme protein/L is used as a blank and corresponds to the contribution from the detergent. Preferably mechanical action is applied during the wash step, e.g. in the form of shaking, rotating or stirring the wash solution with the fabrics. The AMSA wash performance experiments were conducted under the experimental conditions specified below:

TABLE A

| Experimental condition | |
|---|---|
| Detergent | Liquid Model detergent J (see Table B) |
| Detergent dosage | 0.79 g/L |
| Test solution volume | 160 micro L |
| pH | As is |
| Wash time | 20 minutes |
| Temperature | 15° C. or 30° C. |
| Water hardness | 6° dH |
| Enzyme concentration in test | 0.6 mg enzyme protein/L |
| Test material | CS-28 (Rice starch cotton) |

TABLE B

| Model detergent J | | |
|---|---|---|
| Compound | Content of compound (% w/w) | % active component (% w/w) |
| LAS | 5.15 | 5.00 |
| AS | 5.00 | 4.50 |
| AEOS | 14.18 | 10.00 |
| Coco fatty acid | 1.00 | 1.00 |
| AEO | 5.00 | 5.00 |
| MEA | 0.30 | 0.30 |
| MPG | 3.00 | 3.00 |
| Ethanol | 1.50 | 1.35 |

TABLE B-continued

| Model detergent J | | |
|---|---|---|
| Compound | Content of compound (% w/w) | % active component (% w/w) |
| DTPA (as Na5 salt) | 0.25 | 0.10 |
| Sodium citrate | 4.00 | 4.00 |
| Sodium formate | 1.00 | 1.00 |
| Sodium hydroxide | 0.66 | 0.66 |
| $H_2O$, ion exchanged | 58.95 | 58.95 |

Water hardness was adjusted to 6° dH by addition of $CaCl_2$, $MgCl_2$, and $NaHCO_3$ ($Ca^{2+}:Mg^{2+}:HCO_3^-=2:1:4.5$) to the test system. After washing the textiles were flushed in tap water and dried.

TABLE C

| Experimental condition | |
|---|---|
| Detergent | Liquid Model detergent A (see Table D) |
| Detergent dosage | 3.33 g/L |
| Test solution volume | 160 micro L |
| pH | As is |
| Wash time | 20 minutes |
| Temperature | 15° C., 30° C., or 40° C. |
| Water hardness | 15° dH |
| Enzyme concentration in test | 0.6 mg enzyme protein/L |
| Test material | CS-28 (Rice starch cotton) |

TABLE D

| Model detergent A | | |
|---|---|---|
| Compound | Content of compound (% w/w) | % active component (% w/w) |
| LAS | 12.00 | 11.60 |
| AEOS, SLES | 17.63 | 4.90 |
| Soy fatty acid | 2.75 | 2.48 |
| Coco fatty acid | 2.75 | 2.80 |
| AEO | 11.00 | 11.00 |
| Sodium hydroxide | 1.75 | 1.80 |
| Ethanol/Propan-2-ol | 3.00 | 2.70/0.30 |
| MPG | 6.00 | 6.00 |
| Glycerol | 1.71 | 1.70 |
| TEA | 3.33 | 3.30 |
| Sodium formate | 1.00 | 1.00 |
| Sodium citrate | 2.00 | 2.00 |
| DTMPA | 0.48 | 0.20 |
| PCA | 0.46 | 0.18 |
| Phenoxy ethanol | 0.50 | 0.50 |
| $H_2O$, ion exchanged | 33.64 | 33.64 |

Water hardness was adjusted to 15° dH by addition of $CaCl_2$, $MgCl_2$, and $NaHCO_3$ ($Ca^{2+}:Mg^{2+}:HCO_3^-=4:1:7.5$) to the test system. After washing the textiles were flushed in tap water and dried.

TABLE E

| Experimental condition | |
|---|---|
| Detergent | Powder Model detergent X (see Table F) |
| Detergent dosage | 1.75 g/L |
| Test solution volume | 160 micro L |
| pH | As is |
| Wash time | 20 minutes |
| Temperature | 15° C., 30° C., or 40° C. |
| Water hardness | 12° dH |
| Enzyme concentration in test | 0.6 mg enzyme protein/L |
| Test material | CS-28 (Rice starch cotton) |

TABLE F

Model detergent X

| Compound | Content of compound (% w/w) | % active component (% w/w) |
|---|---|---|
| LAS | 16.50 | 15.00 |
| AEO* | 2.00 | 2.00 |
| Sodium carbonate | 20.00 | 20.00 |
| Sodium (di)silicate | 12.00 | 9.90 |
| Zeolite A | 15.00 | 12.00 |
| Sodium sulfate | 33.50 | 33.50 |
| PCA | 1.00 | 1.00 |

*Model detergent X is mixed without AEO. AEO is added separately before wash.

Water hardness was adjusted to 12° dH by addition of $CaCl_2$, $MgCl_2$, and $NaHCO_3$ ($Ca^{2+}:Mg^{2+}:HCO_3^- = 2:1:4.5$) to the test system. After washing the textiles were flushed in tap water and dried.

TABLE G

Experimental condition

| Detergent | Model detergent T (see Table H) |
|---|---|
| Detergent dosage | 5.33 g/L |
| Test solution volume | 160 micro L |
| pH | As is |
| Wash time | 20 minutes |
| Temperature | 15° C., 30° C., or 40° C. |
| Water hardness | 15° dH |
| Enzyme concentration in test | 0.6 mg/L |
| Test material | CS-28 (Rice starch cotton) |

TABLE H

Model detergent T

| Compound | Content of compound (% w/w) | % active component (% w/w) |
|---|---|---|
| LAS, sodium salt | 11.00 | 10.00 |
| AS, sodium salt | 2.00 | 1.80 |
| Soap | 2.00 | 2.00 |
| AEO* | 3.00 | 3.00 |
| Sodium carbonate | 15.15 | 14.90 |
| Sodium (di)silicate | 3.00 | 2.50 |
| Zeolite A | 18.75 | 15.00 |
| HEDP-$Na_4$ | 0.15 | 0.13 |
| Sodium citrate | 2.00 | 2.00 |
| PCA | 1.65 | 1.50 |
| CMC | 2.50 | 1.60 |
| SRP | 0.50 | 0.50 |
| SPC | 22.20 | 20.00 |
| TAED | 3.25 | 3.00 |
| Sodium sulfate | 10.85 | 10.70 |
| Silicone | 2.00 | 2.00 |

*Model detergent T is mixed without AEO. AEO is added separately before wash.

Water hardness was adjusted to 15° dH by addition of $CaCl_2$, $MgCl_2$, and $NaHCO_3$ ($Ca^{2+}:Mg^{2+}:HCO_{3-} = 4:1:7.5$) to the test system. After washing the textiles were flushed in tap water and dried.

General AMSA Automatic Dish Wash Performance Description

A test solution comprising water (6° dH), 4.53 g/L detergent, e.g. Liquid model detergent containing phosphate, as described below, and the polypetide of the invention at concentration of 0 or 0.5 mg enzyme protein/L, is prepared. Melamine plates stained with mixed starch (DM-177 from Center For Test materials BV, P.O. Box 120, 3133 KT, Vlaardingen, The Netherlands) was added and washed for 20 minutes at 15° C. After short rinse under running tap water and drying in the dark, the light intensity values of the stained plates are subsequently measured as a measure for wash performance. The test with 0 mg enzyme protein/L is used as a blank and corresponds to the contribution from the detergent. Preferably mechanical action is applied during the wash step, e.g. in the form of shaking, rotating or stirring the wash solution with the plates. The AMSA automatic dish wash performance experiments were conducted under the experimental conditions specified below:

TABLE I

Experimental condition

| Detergent | Liquid model detergent containing phosphate (see Table J) |
|---|---|
| Detergent dosage | 4.53 g/L |
| Test solution volume | 160 micro L |
| pH | As is |
| Wash time | 20 minutes |
| Temperature | 15° C., 30° C., or 40° C. |
| Water hardness | 6° dH |
| Enzyme concentration in test | 0.5 mg/L |
| Test material | Melamine plates (Mixed Starch) |

TABLE J

Liquid model automatic dish wash detergent containing phosphate

| Compound | Content of compound (% w/w) |
|---|---|
| STPP | 50.0 |
| Sodium carbonate | 20.0 |
| Sodium percarbonate | 10.0 |
| Sodium disilicate | 5.0 |
| TAED | 2.0 |
| Sokalan CP5 (39.5%) | 5.0 |
| Surfac 23-6.5 (100%) | 2.0 |
| Sodium Sulfate | 6.0 |

Water hardness was adjusted to 6° dH by addition of $CaCl_2$, $MgCl_2$, and $NaHCO_3$ ($Ca^{2+}:Mg^{2+}:HCO_3^- = 2:1:4.5$) to the test system. After washing the plates were flushed in tap water and dried.

TABLE K

Experimental condition

| Detergent | Powder model detergent containing phosphate (see Table L) |
|---|---|
| Detergent dosage | 3.33 g/L |
| Test solution volume | 160 micro L |
| pH | As is |
| Wash time | 20 minutes |
| Temperature | 15° C., 30° C., or 40° C. |
| Water hardness | 21° dH |
| Enzyme concentration in test | 0.5 mg/L |
| Test material | Melamine plates (Mixed Starch) |

TABLE L

Powder automatic dish wash model detergent containing phosphate

| Compound | Content of compound (% w/w) |
|---|---|
| $Na_5P_3O_{10}$ | 23.0 |
| Pluronic PE 6800 | 1.0 |
| Sokalan PA 30 | 2.0 |
| ACUSOL 805S | 2.0 |

TABLE L-continued

Powder automatic dish wash model detergent containing phosphate

| Compound | Content of compound (% w/w) |
|---|---|
| Xantan gum | 1.0 |
| Water | 74.0 |

Water hardness was adjusted to 21° dH by addition of $CaCl_2$, $MgCl_2$, and $NaHCO_3$ ($Ca^{2+}$:$Mg^{2+}$:$HCO_3^-$=4:1:10) to the test system. After washing the plates were flushed in tap water and dried.

Evaluation of Wash Performance

The wash performance is measured as the brightness expressed as the intensity of the light reflected from the sample when illuminated with white light. When the sample is stained the intensity of the reflected light is lower, than that of a clean sample. Therefore the intensity of the reflected light can be used to measure wash performance.

Color measurements are made with a professional flatbed scanner (Kodak iQsmart, Kodak) used to capture an image of the washed textile and with a controlled digital imaging system (DigiEye) for capture an image of the washed melamine plates.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int = \sqrt{r^2 + g^2 + b^2}$$

Textile/Melamine:

Textile sample CS-28 (rice starch on cotton) and melamine plates stained with mixed starch (DM-177) are obtained from Center For Testmaterials BV, P.O. Box 120, 3133 KT Vlaardingen, the Netherlands.

Reference Alpha-amylase

The reference alpha-amylase may be the alpha-amylase of SEQ ID NO: 3.

The present invention is further described by the following examples that should not be construed as limiting the scope of the invention.

EXAMPLES

Example 1

Amylase Activity using Amylazyme Assay

The amylase activity of the variants of the present invention was determined by the Amylazyme assay as described herein.

The amylases were expressed from *B.subtilis* host strains by fermenting in a deep well micro titer plate with 1 ml fermentation media in each well. They were incubated at 37° C. for 3 days under vigorous shaking at 600 rpm.

Fermentation Media

| Chemical name | Supplier | Lot no | For 1 liter |
|---|---|---|---|
| di-Ammonium hydrogen phosphate | $(NH_4)_2HPO_4$ | Merck 1207 | 6 g |
| Potato protein (7.5%) | | (Avebe TAK) | 26 ml |

-continued

| Chemical name | | Supplier | Lot no | For 1 liter |
|---|---|---|---|---|
| Magnesium sulfate | $MgSO_4 \cdot 7H_2O$ | Merck 5886 | | 1.2 g |
| Potassium di-hydrogen phosphate | $KH_2PO_4$ | Merck 4873 | | 12 g |
| di-Sodium hydrogen phosphate | $Na_2HPO_4 \cdot 2H_2O$ | Merck 6580 | | 5 g |
| Micro PM Low MSA-SUB-FS-0516 | | | | 18 ml |
| Potassium sulfate | $K_2SO_4$ | Merck 5153 | | 1.8 g |
| Calcium chloride $2H_2O$ | $CaCl_2 \cdot 2H_2O$ | Merck 2382 | | 0.1 g |
| Soluble starch | | Merck 1253 | | 33 g |
| SB 2121 | | | 101-8523 | 0.5 ml |
| Water add to | | | | 1000 ml |

The supernatants from the fermentations were diluted 100 fold in assay buffer (100 mM B&R buffer pH 7,3 with 0,12mM $CaCl_2$ and 0,01% brij) prior to measuring the activity using the Amylazyme assay. The Amylazyme tablets were also dissolved in the assay buffer.

TABLE 1

Activity of the variants of the invention

| Amylase | Activity (average) |
|---|---|
| SEQ ID NO: 3 | 1.9 |
| T269N | 1.4 |
| T269Y | 1.8 |
| T269G | 1.8 |
| M294Y | 1.4 |
| M109A | 0.4 |
| M109G | 1.3 |
| M109H | 1.3 |
| M109L | 1.5 |

As can be seen from Table 1, all tested variants maintain the amylase activity. Average activity values above 0 indicate that the variant show alpha-amylase activity. The reference used herein is the polypeptide according to SEQ ID NO:3. Activity of the supernatant does not reflect the wash performance of the isolated, i.e. purified, enzymes. Thus, these data does not indicate the wash performance. Furthermore, the data has not been normalized according to protein concentration used in the experiment. Accordingly, the data shows that all tested variants maintain the amylase activity.

Example 2

Amylase Activity using Phadebas Assay

The amylase activity of the variants of the present invention was determined by the Phadebas assay as described herein.

The amylases were expressed from *B. subtilis* host strains by fermenting in a deep well micro titer plate with 1 ml fermentation media from Example 1 in each well. They were incubated at 37° C. for 3 days under vigorous shaking at 600 rpm.

The supernatants were diluted 100× in assay buffer (100 mM B&R buffer pH 7,3 with 0.12 mM $CaCl_2$ and 0,01% brij) prior to measuring the activity using the Phadebas assay. The Phadebas tablets were also dissolved in the assay buffer.

TABLE 2

Activity of the variants of the invention

| Amylase | Activity (average) |
|---|---|
| SEQ ID NO: 3 | 1.7 |
| Q51T + M109G + N193F + G201Y | 0.5 |
| Q51T + M109G + N193F + G201Y + T269N + M294Y + Q297Y + A298N + N314G | 0.4 |
| M109G + G201Y | 0.6 |
| M109A + G201F | 0.3 |
| M294N | 1.7 |
| Q51D + M109H | 0.3 |
| M109L + M200L | 0.9 |

As can be seen from Table 2, all tested variants maintain the amylase activity. Average activity values above 0 indicate that the variant show alpha-amylase activity. The reference used herein is the polypeptide according to SEQ ID NO:3. Activity of the supernatant does not reflect the wash performance of the isolated, i.e. purified, enzymes. Thus, these data does not indicate the wash performance.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Sequences—bold and underlined parts of the sequences indicate the predicted signal sequence of the polypeptide.

| SEQ ID NO: | Sequence |
|---|---|
| 1 | ATGAAAATCCGCAACGGTTGGAAAAAAACCTTGACGCTGTTATTTGCGTCATCTTC<br>TTGCTGCCTCATTCTGCAGCCGCGACCTTTGCCGGGGACAACGGCACGATGATG<br>CAATACTTTGAATGGTATCTGCCCAACGACGGGACGCTTTGGACCAAGATGGGCA<br>GCGACGCGTCGCACCTGAAGTCGATCGGGATCACCGGCGTCTGGTTCCCGCCG<br>GCGTACAAAGGCCAATCGCAGTCGGACGTCGGCTACGGCGTATACGACATGTAC<br>GACCTCGGCGAATTCAACCAAAAAGGAACCGTCCGCACCAAGTACGGCACCAAA<br>GCCCAGCTCCAATCGGCGATCACCTCCCTGCACAACAACGGCATCCAAGCCTAC<br>GGGGACGTCGTCCTCAACCACCGCATGGGCGCCGATGCGACGGAGACGATCTC<br>CGCCGTGGAAGTCAACCCGTCCAACCGCAACCAAGTCACCTCCGGGGCTTACAA<br>CATCTCCGCTTGGACCGACTTCGAATTCCCGGGCCGCGGCAACACCTACTCCTC<br>GTTTAAGTGGCACTCCTACTACTTTGACGGCGTGGACTGGGACCAATCCCGCCA<br>GCTGAGCGGCAAGATCTACCAGATCCAAGGCACCGGCAAAGCGTGGGACTGGG<br>AAGTCGATTCCGAAAACGGCAACTACGACTACCTGATGGGCGCGGACATCGACT<br>ACGACCACCCGGACGTGCAAACGGAAGTGAAGAACTGGGGCAAGTGGTTCGTCA<br>ACACCCTCAACCTCGACGGCGTGCGCCTCGACGCGGTCAAGCACATCAAGTTCG<br>ACTACATGTCTTCCTGGCTGTCCAGCGTCAAATCCACGACCGGCAAGTCCAACCT<br>GTTCGCCGTCGGCGAATACTGGAACACCTCGCTCGGAGCGCTGGAGAACTACGA<br>GAACAAAACCAACTGGAGCATGTCGCTGTTCGACGTGCCGCTGCACATGAACTTC<br>CAAGCGGCAGCGAACGGCGGCGGCTACTATGATATGCGCAACCTGCTCAACAAC<br>ACGATGATGAAAAATCACCCGATCCAAGCGGTCACCTTCGTCGACAACCACGACA<br>CCGAGCCG<br>GGCCAAGCCCTGCAATCGTGGGTATCCGACTGGTTCAAACCGCTGGCCTACGCG<br>ACGATCCTGACCCGTCAAGAAGGCTACCCGTGCGTGTTCTACGGCGACTACTAC<br>GGCATCCCGTCGCAAAGCGTCTCCGCGAAATCCACCTGGTTGGACAAGCAGCTT<br>TCCGCACGCAAATCCTACGCGTACGGCACCCAGCACGACTACTTGGACAACCAA<br>GACGTGATCGGCTGGACGCGCGAAGGCGATTCCGCGCACGCGGGCTCGGGTCT<br>TGCCACCGTCATGTCGGACGGCCCTGGCGGCTCCAAGACGATGTACGTCGGCAC<br>CGCCCATGCCGGCCAAGTCTTCAAGGACATCACCGGCAACCGCACCGACACCGT<br>CACGATCAACTCCGCAGGCAACGGCACCTTCCCCTGCAACGGCGGCTCCGTCTC<br>GATCTGGGTCAAACAA |
| 2 | MKIRNGWKKTLTLLFALIFLLPHSAAATFAGDNGTMMQYFEWYLPNDGTLWTKMGS<br>DASHLKSIGITGVWFPPAYKGQSQSDVGYGVYDMYDLGEFNQKGTVRTKYGTKAQL<br>QSAITSLHNNGIQAYGDVVLNHRMGADATETISAVEVNPSNRNQVTSGAYNISAWTD<br>FEFPGRGNTYSSFKWHSYYFDGVDWDQSRQLSGKIYQIQGKAWDWEVDSENGNYD<br>YLMGADIDYDHPDVQTEVKNWGKWFVNTLNLDGVRLDAVKHIKFDYMSSWLSSVKS<br>TTGKSNLFAVGEYWNTSLGALENYENKTNWSMSLFDVPLHMNFQAAANGGGYYDM<br>RNLLNNTMMKNHPIQAVTFVDNHDTEPGQALQSWVSDWFKPLAYATILTRQEGYPC<br>VFYGDYYGIPSQSVSAKSTWLDKQLSARKSYAYGTQHDYLDNQDVIGWTREGDSAH<br>AGSGLATVMSDGPGGSKTMYVGTAHAGQVFKDITGNRTDTVTINSAGNGTFPCNGG<br>SVSIWVKQ |
| 3 | TFAGDNGTMMQYFEWYLPNDGTLWTKMGSDASHLKSIGITGVWFPPAYKGQSQSD<br>VGYGVYDMYDLGEFNQKGTVRTKYGTKAQLQSAITSLHNNGIQAYGDVVLNHRMGA<br>DATETISAVEVNPSNRNQVTSGAYNISAWTDFEFPGRGNTYSSFKWHSYYFDGVDW<br>DQSRQLSGKIYQIQGKAWDWEVDSENGNYDYLMGADIDYDHPDVQTEVKNWGKVVF<br>VNTLNLDGVRLDAVKHIKFDYMSSWLSSVKSTTGKSNLFAVGEYWNTSLGALENYE<br>NKTNWSMSLFDVPLHMNFQAAANGGGYYDMRNLLNNTMMKNHPIQAVTFVDNHD<br>TEPGQALQSWVSDWFKPLAYATILTRQEGYPCVFYGDYYGIPSQSVSAKSTWLDKQ<br>LSARKSYAYGTQHDYLDNQDVIGWTREGDSAHAGSGLATVMSDGPGGSKTMYVG<br>TAHAGQVFKDITGNRTDTVTINSAGNGTFPCNGGSVSIWVKQ |
| 4 | AQSVPWGISRVQAPAAHNRGLTGSGVKVAVLDTGISTHPDLNIRGGASFVPGEPST<br>QDGNGHGTHVAGTIAALNNSIGVLGVAPSAELYAVKVLGASGSGSVSSIAQGLEWA<br>GNNGMHVANLSLGSPSPSATLEQAVNSATSRGVLVVAASGNSGAGSISYPARYANA<br>MAVGATDQNNNRASFSQYGAGLDIVAPGVNVQSTYPGSTYASLNGTSMATPHVAG<br>AAALVKQKNPSWSNVQIRNHLKNTATSLGSTNLYGSGLVNAEAATR |

| SEQ ID NO: | Sequence |
|---|---|
| 5 | EVSQDLFNQFNLFAQYSAAAYCGKNNDAPAGTNITCTGNACPEVEKADATFLYSFED<br>SGVGDVTGFLALDNTNKLIVLSFRGSRSIENWIGNLNFDLKEINDICSGCRGHDGFTS<br>SWRSVADTLRQKVEDAVREHPDYRVVFTGHSLGGALATVAGADLRGNGYDIDVFSY<br>GAPRVGNRAFAEFLTVQTGGTLYRITHTNDIVPRLPPREFGYSHSSPEYWIKSGTLVP<br>VTRNDIVKIEGIDATGGNNQPNIPDIPAHLWYFGLIGTCL |
| 6 | HHNGTNGTMMQYFEWYLPNDGNHWNRLRSDASNLKDKGISAVWIPPAWKGASQN<br>DVGYGAYDLYDLGEFNQKGTIRTKYGTRNQLQAAVNALKSNGIQVYGDVVMNHKGG<br>ADATEMVRAVEVNPNNRNQEVSGEYTIEAWTKFDFPGRGNTHSNFKWRWYHFDGV<br>DWDQSRKLNNRIYKFRGDGKGWDWEVDTENGNYDYLMYADIDMDHPEVVNELRN<br>WGVWYTNTLGLDGFRIDAVKHIKYSFTRDWINHVRSATGKNMFAVAEFWKNDLGAIE<br>NYLNKTNWNHSVFDVPLHYNLYNASKSGGNYDMRQIFNGTVVQRHPMHAVTFVDN<br>HDSQPEEALESFVEEWFKPLAYALTLTREQGYPSVFYGDYYGIPTHGVPAMKSKIDP<br>ILEARQKYAYGRQNDYLDHHNIIGWTREGNTAHPNSGLATIMSDGAGGNKWMFVGR<br>NKAGQVWTDITGNRAGTVTINADGWGNFSVNGGSVSIWVNK |
| 7 | HHNGTNGTMMQYFEWHLPNDGNHWNRLRDDASNLRNRGITAIWIPPAWKGTSQND<br>VGYGAYDLYDLGEFNQKGTVRTKYGTRSQLESAIHALKNNGVQVYGDVVMNHKGGA<br>DATENVLAVEVNPNNRNQEISGDYTIEAWTKFDFPGRGNTYSDFKWRWYHFDGVD<br>WDQSRQFQNRIYKFRGDGKAWDWEVDSENGNYDYLMYADVDMDHPEVVNELRRW<br>GEWYTNTLNLDGFRIDAVKHIKYSFTRDWLTHVRNATGKEMFAVAEFWKNDLGALEN<br>YLNKTNWNHSVFDVPLHYNLYNASNSGGNYDMAKLLNGTVVQKHPMHAVTFVDNH<br>DSQPGESLESFVQEWFKPLAYALILTREQGYPSVFYGDYYGIPTHSVPAMKAKIDPIL<br>EARQNFAYGTQHDYFDHHNIIGWTREGNTTHPNSGLATIMSDGPGGEKWMYVGQN<br>KAGQVWHDITGNKPGTVTINADGWANFSVNGGSVSIWVKR |
| 8 | NTAPINETMMQYFEWDLPNDGTLWTKVKNEAANLSSLGITALWLPPAYKGTSQSDV<br>GYGVYDLYDLGEFNQKGTIRTKYGTKTQYIQAIQAAKAAGMQVYADVVFNHKAGADG<br>TEFVDAVEVDPSNRNQETSGTYQIQAWTKFDFPGRGNTYSSFKWRWYHFDGTDWD<br>ESRKLNRIYKFRSTGKAWDWEVDTENGNYDLMFADLDMDHPEVVTELKNWGTWY<br>VN<br>TTNIDGFRLDAVKHIKYTFFPDWLTYVRNQTGKNLFAVGEFWSYDVNKLHNYITKTNG<br>SMSLFDAPLHNNFYTASKSSGYFDMRYLLNNTLMKDQPSLAVTLVDNHDTQPGQSL<br>QSWVEPWFKPLAYAFILTRQEGYPCVFYGDYYGIPKYNIPGLKSKIDPLLIARRDYAYG<br>TQRDYIDHQDIIGWTREGIDTKPNSGLAALITDGPGGSKWMYVGKKHAGKVFYDLTG<br>NRSDTVTINADGWGEFKVNGGSVSIWVAK |
| 9 | AATNGTMMQYFEWYVPNDGQQWNRLRTDAPYLSSVGITAVWTPPAYKGTSQADVG<br>YGPYDLYDLGEFNQKGTVRTKYGTKGELKSAVNTLHSNGIQVYGDVVMNHKAGADY<br>TENVTAVEVNPSNRNQETSGEYNIQAWTGFNFPGRGTTYSNFKWQWFHFDGTDWD<br>QSRSLSRIFKFRGTGKAWDWEVSSENGNYDYLMYADIDYDHPDVVNEMKKWGVWY<br>ANEVGLDGYRLDAVKHIKFSFLKDWVDNARAATGKEMFTVGEYWQNDLGALNNYLA<br>KVNYNQSLFDAPLHYNFYAASTGGGYYDMRNILNNTLVASNPTKAVTLVENHDTQPG<br>QSLESTVQPWFKPLAYAFILTRSGGYPSVFYGDMYGTKGTTTREIPALKSKIEPLLKA<br>RKDYAYGTQRDYIDNPDVIGWTREGDSTKAKSGLATVITDGPGGSKRMYVGTSNAG<br>EIWYDLTGNRTDKITIGSDGYATFPVNGGSVSVWVQQ |
| 10 | HHNGTNGTMMQYFEWYLPNDGNHWNRLNSDASNLKSKGITAVWIPPAWKGASQND<br>VGYGAYDLYDLGEFNQKGTVRTKYGTRSQLQAAVTSLKNNGIQVYGDVVMNHKGGA<br>DATEMVRAVEVNPNNRNQEVTGEYTIEAWTRFDFPGRGNTHSSFKWRWYHFDGVD<br>WDQSRRLNNRIYKFRGHGKAWDWEVDTENGNYDYLMYADIDMDHPEVVNELRNW<br>GVWYTNTLGLDGFRIDAVKHIKYSFTRDWINHVRSATGKNMFAVAEFWKNDLGAIEN<br>YLQKTNWNHSVFDVPLHYNLYNASKSGGNYDMRNIFNGTVVQRHPSHAVTFVDNHD<br>SQPEEALESFVEEWFKPLAYALTLTREQGYPSVFYGDYYGIPTHGVPAMRSKIDPILE<br>ARQKYAYGKQNDYLDHHNIIGWTREGNTAHPNSGLATIMSDGAGGSKWMFVGRNK<br>AGQVWSDITGNRTGTVTINADGWGNFSVNGGSVSIWVNK |
| 11 | HHNGTNGTMMQYFEWYLPNDGNHWNRLNSDASNLKSKGITAVWIPPAWKGASQND<br>VGYGAYDLYDLGEFNQKGTVRTKYGTRSQLQAAVTSLKNNGIQVYGDVVMNHKGGA<br>DATEMVRAVEVNPNNRNQEVTGEYTIEAWTRFDFPGRGNTHSSFKWRWYHFDGVD<br>WDQSRRLNNRIYKFRGKAWDWEVDTENGNYDLMYADIDMDHPEVVNELRNWGV<br>WYTNTLGLDGFRIDAVKHIKYSFTRDWINHVRSATGKNMFAVAEFWKNDLGAIENYL<br>QKTNWNHSVFDVPLHYNLYNASKSGGNYDMRNIFNGTVVQRHPSHAVTFVDNHDS<br>QPEEALESFVEEWFKPLAYALTLTREQGYPSVFYGDYYGIPTHGVPAMRSKIDPILEA<br>RQKYAYGPQHDYLDHPDVIGWTREGDSSHPKSGLATLITDGPGGSKRMYAGLKNAG<br>ETWYDITGNRSDTVKIGSDGWGEFHVNDGSVSIYVQK |
| 12 | HHNGTNGTMMQYFEWYLPNDGNHWNRLRSDASNLKDKGITAVWIPPAWKGASQND<br>VGYGAYDLYDLGEFNQKGTVRTKYGTRNQLQAAVTALKSNGIQVYGDVVMNHKGGA<br>DATEWVRAVEVNPSNRNQEVSGDYTIEAWTKFDFPGRGNTHSNFKWRWYHFDGVD<br>WDQSRQLQNRIYKFRGDGKGWDWEVDTENGNYDYLMYADIDMDHPEVVNELRNW<br>GVWYTNTLGLDGFRIDAVKHIKYSFTRDWLTHVRNTTGKNMFAVAEFWKNDIGAIEN<br>YLSKTNWNHSVFDVPLHYNLYNASRSGGNYDMRQIFNGTVVQRHPTHAVTFVDNHD<br>SQPEEALESFVEEWFKPLACALTLTRDQGYPSVFYGDYYGIPTHGVPAMKSKIDPILE<br>ARQKYAYGKQNDYLDHHNMIGWTREGNTAHPNSGLATIMSDGPGGNKWMYVGRN<br>KAGQVWRDITGNRSGTVTINADGWGNFSVNGGSVSIWVNN |

| SEQ ID NO: | Sequence |
|---|---|
| 13 | TFAGDNGTMMQYFEWYLPNDGTLWTKMGSDASHLKSIGITGVWFPPAYKGQSQSD VGYGVYDMYDLGEFNQKGTVRTKYGTKAQLQSAITSLHNNGIQAYGDVVLNHRMGA DATETISAVEVNPSNRNQVTSGAYNISAWTDFEFPGRGNTYSSFKWHSYYFDGVDW DQSRQLSGKIYQIQGTGKAWDWEVDSENGNYDYLMGADIDYDHPDVQTEVKNWGK WFVNTLNLDGVRLDAVKHIKFDYMSSWLSSVKSTTGKSNLFAVGEYWNTSLGALEN YENKTNWSMSLFDVPLHMNFQAAANGGGYYDMRNLLNNTMMKNHPIQAVTFVDNH DTEPGQALQSWVSDWFKPLAYATILTRQEGYPCVFYGDYYGIPSQSVSAKSTWLDK QLSARKSYAYGTQHDYLDNQDVIGWTREGDSAHAGSGLATVMSDGPGGSKTMYVG TAHAGQVFKDITGNRTDTVTINSAGNGTFPCNGGSVSIWVKQ |

The invention claimed is:

1. An alpha-amylase variant of a parent alpha-amylase, comprising a substitution at one or more positions corresponding to positions 109, 51, 201, 269, 294, 297, 298, 193, and 314 of the polypeptide according to SEQ ID NO:3, wherein said variant has alpha-amylase activity, and wherein said parent alpha-amylase has at least 90% sequence identity to the polypeptide of SEQ ID NOs: 3 or 13.

2. The variant according to claim 1, which is a variant of a parent alpha-amylase selected from the group consisting of:
   a. a polypeptide having at least 90% sequence identity to the polypeptide of SEQ ID NOs: 3 or 13;
   b. a polypeptide encoded by a polynucleotide that hybridizes under high stringency conditions with (i) the mature polynucleotide coding sequence of SEQ ID NO: 1, or (ii) the full-length complement of (i), wherein the high stringency conditions are defined as prehybridization and hybridization at 42 degrees centigrade in 5×SSPE, 0.3 percent SDS, 200 micrograms/ml sheared and denatured salmon sperm DNA, and 50 percent formamide for 12 to 24 hours, and washing three times each for 15 minutes using 2×SSC, 0.2 percent SDS at 65 degrees centigrade;
   c. a polypeptide encoded by a polynucleotide having at least 90% sequence identity to the mature polynucleotide coding sequence of SEQ ID NO:1; and
   d. a fragment of the polypeptide of SEQ ID NOs: 3 or 13, which has alpha-amylase activity.

3. The variant according to claim 1, which has at least 90%, but less than 100% sequence identity to the polypeptide according to SEQ ID NOs: 3 or 13.

4. The variant according to claim 1, wherein the number of substitutions is 1 to 20.

5. The variant according to claim 1, which comprises a substitution at one position corresponding to any one of positions 109, 51, 201, 269, 294, 297, 298, 193, and 314 of the polypeptide of SEQ ID NO: 3.

6. The variant according to claim 5, wherein the substitution is selected from the list consisting of;
   i. Q51T, Q51A, Q51R, Q51N, Q51D, Q51C, Q51E, Q51G, Q51H, Q51I, Q51L, Q51K, Q51M, Q51F, Q51P, Q51S, Q51W, Q51Y, or Q51V;
   ii. M109G, M109A, M109H, M109L, M109R, M109N, M109D, M109C, M109E, M109Q, M109I, M109K, M109F, M109P, M109S, M109T, M109W, M109Y, or M109V;
   iii. N193F, N193A, N193R, N193D, N193C, N915E, N193Q, N193G, N193H, N193I, N193L, N193K, N193M, N193P, N193S, N193T, N193W, N193Y, or N193V;
   iv. G201Y, G201A, G201R, G201D, G201C, G201E, G201Q, G201H, G201I, G201L, G201K, G201M, G201N, G201P, G201S, G201T, G201W, G201Y, or G201V;
   v. T269N, T269Y, T269G, T269A, T269R, T269D, T269C, T269E, T269F, T269Q, T269H, T269I, T269L, T269K, T269M, T269P, T269S, T269W, or T269V;
   vi. M294Y, M294N, M294A, M294R, M294D, M294C, M294E, M294Q, M294G, M294F, M294H, M294I, M294L, M294K, M294P, M294S, M294T, M294W, or M294V;
   vii. Q297Y, Q297A, Q297R, Q297N, Q297D, Q297C, Q297E, Q297G, Q297H, Q297I, Q297L, Q297K, Q297M, Q297F, Q297P, Q297S, Q297T, Q297W, or Q297V;
   viii. A298N, A298R, A298D, A298C, A298E, A298Q, A298G, A298H, A298I, A298L, A298K, A298M, A298F, A298P, A298S, A298T, A298W, A298Y, or A298V; or
   ix. N314G, N314A, N314R, N314D, N314C, N314E, N314Q, N314H, N314I, N314L, N314K, N314M, N314F, N314P, N314S, N314T, N314W, N314Y, or N314V,
wherein each position corresponds to the corresponding position in the polypeptide of SEQ ID NO: 3.

7. The variant according to claim 1, which comprises a substitution at two positions corresponding to any one of positions 109, 51, 201, 269, 294, 297, 298, 193, and 314 of the polypeptide of SEQ ID NO:3.

8. The variant according to claim 7, wherein said variant comprises a substitution at each position corresponding to positions;
   (i) 51 and 109;
   (ii) 109 and 201;
   (iii) 269 and 294; or
   (iv) 294 and 297;
wherein each position corresponds to the corresponding positions in the polypeptide of SEQ ID NO: 3.

9. The variant according to claim 1, which comprises a substitution at three positions corresponding to any of positions 109, 51, 201, 269, 294, 297, 298, 193, and 314 of the polypeptide of SEQ ID NO:3.

10. The variant according to claim 1, wherein the variant comprises a substitution at each positions corresponding to positions;
   (i) 51, 109, 193, and 201;
   (ii) 109, 201, 269, and 294;
   (iii) 201, 269, 294 and 297; or
   (iv) 51, 109, 193, 201, 269, 294, 297, 298, and 314;
wherein each position corresponds to the corresponding positions in the polypeptide of SEQ ID NO: 3.

11. The variant according to claim 1, which further comprises an alteration at positions corresponding to positions;
   105L,I,F+206Y; 105L,I+206Y+217I; 105F+206Y+208Y+217V+246V; 105L+206F; 105I+206Y+208Y+217I+246V; 195F+213S+214T; 195F+206Y+208Y+213T+214T+217M,V; 195F+206Y+208F,L+213T+214T+217V; 195F+206Y+213S+214T; 195F+206Y+208Y+213S+214T+217M; 195F+206Y+208F+213T+214T+217M; 195F+206Y+208Y+213T+214T+217Q; 195F+206Y+213G+214T; 195F+206Y+213S; 195F+206Y+208Y+213T+214T+217M; 195F+213S; 195F+206Y+208L+213T+214T+217M; 195F+213G+214T; 206Y,F+208Y+217Q; 206Y+208Y+217I; 206F+208Y+217M; 206Y+208Y; 206Y+217M; 206Y+208Y+213A+217M; 206Y+208Y+217V+246V; 206Y+213G; 206Y+208F+217V; 206N+208Y+217M; 206F+208Y+217V; 206Y+246V; 206Y+217I,V; 206F+208F+217I; 206Y+208L+213S; 206F+217I; 206Y+217I+246I; 206L+217V; 206Y+208F+217H; 206L+208F+217I; 206L+217V+246L; 206F+246V; 208Y+213S+217M; 208Y+213A+217Q; 63I+206Y; 63I+206Y+241V; 63V+206Y; 63V+105L+206Y; 63V+206Y+217I; 63V+105F+206Y+208F+217I; 63V+206Y+246V; 63V+206F; 63V+206L+217V; 63V+105F+206Y; 63V+206Y+241V+246L; 195F+206Y+208Y+214T+217V; 186E+195F+206Y; 195F+206Y+208Y+213T+217V; 186E+195F+202T+206Y+209S; 63I+195F+206Y+210S; 195F+206Y+213P+214T; 195F+206Y+208Y+213T+214T+217I; 186E+195F+206Y+210S; 195F+213P; 186E+195F+202T+206Y+210S; 195F+206H; 195F+208Y+213T+214T+217V; 206Y+208Y+213T+214T+217V; 195F+206Y+217V; 195F+206Y+208Y+213S+214T; 195F+206Y+208Y; 195F+213I+214P; 195F+206Y+208Y+213T+214T; 195F+206Y; 206Y+213S; 182P+186E; 182S+186E; 182V+186K; 179L+186H+190P; 179L+186K,R,S+190P; 179L+190P; 179L+182C+186K+190P; 179L+182P+186S,V+190P; 179L+182S+186Q+190P; 173F+174Q; 173Y+174S; 172K+173Y+174E; 193A,D,N,S+195F; 213A+214Q; 213P+214L; 213S+214R; 48V+60V; 213G+214T; 213I+214P; 213N+214I; 213N+214Q, and 213P,S+214T, wherein numbering is according to SEQ ID NO:11.

12. The variant according to claim 1, wherein said variant comprises a pairwise deletion selected from the list consisting of:
   181 and 182;
   181 and 183;
   181 and 184;
   182 and 183;
   182 and 184; and
   183 and 184;
wherein the positions correspond to the positions of SEQ ID NO: 13.

13. The variant according to claim 1, which has an improved stability in detergent compositions relative to the parent alpha-amylase of SEQ ID NOs: 3 or 13.

14. The variant according to claim 1, which has an improved performance in detergent compositions relative to the parent alpha-amylase of SEQ ID NOs: 3 or 13.

15. The variant according to claim 14, wherein the improved performance is determined according to an Automatic Mechanical Stress Assay (AMSA).

16. The variant according to claim 13, wherein the detergent composition is a liquid detergent composition, a powder detergent composition, a unit dose detergent composition, or a soap bar detergent composition.

17. A composition comprising an alpha-amylase variant according to claim 1.

18. The composition according to claim 17, further comprising at least one further active component.

19. The composition according to claim 16, wherein said further active component is an enzyme selected from a protease, lipase, cellulase, pectate lyase and mannanase.

20. The composition according to claim 19, wherein the enzyme is selected from the group consisting of:
   (i) a protease comprising one or more modifications in the following positions: 32, 33, 48-54, 58-62, 94-107, 116, 123-133, 150, 152-156, 158-161, 164, 169, 175-186, 197, 198, 203-216 as compared with the protease in SEQ ID NO:4;
   (ii) a lipase comprising one or more modifications in the following positions: 1-5, 27, 33, 38, 57, 91, 94, 96, 97, 111, 163, 210, 225, 231, 233, 249, and 254-256 as compared with the lipase in SEQ ID NO:5;
   (iii) an alpha-amylase comprising one or more modifications in the following positions: 9, 118, 149, 182, 186, 195, 202, 257, 295, 299, 320, 323, A339, 345, and 458 as compared with the alpha-amylase in SEQ ID NO:6;
   (iv) an alpha-amylase comprising one or more modifications in the following positions: 140, 195, 206, 243, 260, and 476 as compared with the alpha-amylase in SEQ ID NO:7;
   (v) an alpha-amylase comprising one or more modifications in the following positions: 180, 181, 243, and 475 as compared with the alpha-amylase in SEQ ID NO:8;
   (vi) an alpha-amylase comprising one or more modifications in the following positions: 178, 179, 187, 203, 458, 459, 460, and 476 as compared with the alpha-amylase in SEQ ID NO:9;
   (vii) an alpha-amylase comprising a modifications in the following position: 202 as compared with the alpha-amylase in SEQ ID NO:10;
   (viii) an alpha-amylase comprising one or more modifications in the following positions: 405, 421, 422, and 428 as compared with the alpha-amylase in SEQ ID NO:11; and/or
   (ix) an alpha-amylase according to SEQ ID NO:12.

21. The composition according to claim 15, which is a detergent composition.

22. The composition according to claim 17, which is a liquid laundry or liquid dish wash composition, a powder laundry composition, or powder dish wash composition.

23. A polynucleotide encoding the variant according to claim 1.

24. A nucleic acid construct comprising the polynucleotide according to claim 23.

25. An expression vector comprising the polynucleotide according to claim 24.

26. An isolated host cell comprising the polynucleotide according to claim 23, the nucleic acid construct according to claim 24, or the expression vector according to claim 25.

27. A method of producing an alpha-amylase variant, comprising:

a. cultivating the host cell of claim 26 under conditions suitable for expression of the variant; and b. recovering said variant.

28. A method for obtaining an alpha-amylase variant, comprising introducing into a parent alpha-amylase having at least 90% sequence identity to the polypeptide of SEQ ID NOs: 3 or 13 a substitution at one or more positions said substitutions corresponding to positions 109, 51, 201, 269, 294, 297, 298, 193, and 314 of SEQ ID NO:3, wherein the variant has at least 90%, but less than 100% sequence identity with the amino acid sequence of SEQ ID NOs: 3 or 13, wherein the variant has alpha-amylase activity; and recovering said variant.

29. A method of improving the detergent stability of a parent alpha-amylase having the amino acid sequence of SEQ ID NOs: 3 or 13, or having at least 90% sequence identity thereto, said method comprising the steps of:

a) a substitution at one or more positions said substitutions corresponding to positions 109, 51, 201, 269, 294, 297, 298, 193, and 314 of SEQ ID NO:3, wherein the variant has at least 90%, but less than 100% sequence identity with the amino acid sequence of SEQ ID NOs: 3 or 13, wherein the variant has alpha-amylase activity; and b) introducing into the parent alpha-amylase one or more of the following substitutions; 105L,I,F+206Y; 105L,I+206Y+217I; 105F+206Y+208Y+217V+246V; 105L+206F; 105I+206Y+208Y+217I+246V; 195F+213S+214T; 195F+206Y+208Y+213 T+214T+217M,V; 195F+206Y+208F,L+213T+214T+217V; 195F+206Y+213S+214T; 195F+206Y+208Y+213S+214T+217M; 195F+206Y+208F+213T+214T+217M; 195F+206Y+208Y+213T+214T+217Q; 195F+206Y+213G+214T; 195F+206Y+213S; 195F+206Y+208Y+213T+214T+217M; 195F+213S; 195F+206Y+208L+213T+214T+217M; 195F+213G+214T; 206Y,F+208Y+217Q; 206Y+208Y+217I; 206F+208Y+217M; 206Y+208Y; 206Y+217M; 206Y+208Y+213A+217M; 206Y+208Y+217V+246V; 206Y+213G; 206Y+208F+217V; 206N+208Y+217M; 206F+208Y+217V; 206Y+246V; 206Y+217I,V; 206F+208F+217I; 206Y+208L+213S; 206F+217I; 206Y+217I+246I; 206L+217V; 206Y+208F+217H; 206L+208F+217I; 206L+217V+246L; 206F+246V; 208Y+213S+217M; 208Y+213A+217Q; 63I+206Y; 63I+206Y+241V; 63V+206Y; 63V+105L+206Y; 63V+206Y+217I; 63V+105F+206Y+208F+217I; 63V+206Y+246V; 63V+206F; 63V+206L+217V; 63V+105F+206Y; 63V+206Y+241V+246L; 195F+206Y+208Y+214T+217V; 186E+195F+206Y; 195F+206Y+208Y+213T+217V; 186E+195F+202T+206Y+209S; 63I+195F+206Y+210S; 195F+206Y+213P+214T; 195F+206Y+208Y+213T+214T+217I; 186E+195F+206Y+210S; 195F+213P; 186E+195F+202T+206Y+210S; 195F+206H; 195F+208Y+213T+214T+217V; 206Y+208Y+213T+214T+217V; 195F+206Y+217V; 195F+206Y+208Y+213S+214T; 195F+206Y+208Y; 195F+213I+214P; 195F+206Y+208Y+213T+214T; 195F+206Y; 206Y+213S; 182P+186E; 182S+186E; 182V+186K; 179L+186H+190P; 179L+186K,R,S+190P; 179L+190P; 179L+182C+186K+190P; 179L+182P+186S,V+190P; 179L+182S+186Q+190P; 173F+174Q; 173Y+174S; 172K+173Y+174E; 193A,D,N,S+195F; 213A+214Q; 213P+214L; 213S+214R; 48V+60V; 213G+214T; 213I+214P; 213N+214I; 213N+214Q, and 213P,S+214T, wherein numbering is according to SEQ ID NO:11, wherein the variant has at least 90%, but less than 100% sequence identity with the polypeptide of SEQ ID NOs: 3 or 13, and wherein the variant has alpha-amylase activity and improved detergent stability and/or improved performance compared to the parent alpha-amylase.

30. The method according to claim 27, wherein the variant has at least 50% of the activity of the parent alpha-amylase having the amino acid sequence of SEQ ID NOs: 3 or 13.

31. The method according to claim 27, wherein the activity is determined according to a Phadebas assay.

\* \* \* \* \*